(12) United States Patent
Hou et al.

(10) Patent No.: US 9,890,184 B2
(45) Date of Patent: Feb. 13, 2018

(54) COMPLEX AND USE OF SAME

(71) Applicant: RIKEN, Saitama (JP)

(72) Inventors: Zhaomin Hou, Saitama (JP); Takanori Shima, Saitama (JP); Shaowei Hu, Saitama (JP); Yoshinori Endo, Saitama (JP)

(73) Assignee: RIKEN, Saitama (JP)

( * ) Notice: Subject to any disclaimer, the term of this patent is extended or adjusted under 35 U.S.C. 154(b) by 176 days.

(21) Appl. No.: 14/443,888

(22) PCT Filed: Nov. 20, 2013

(86) PCT No.: PCT/JP2013/081276
§ 371 (c)(1),
(2) Date: May 19, 2015

(87) PCT Pub. No.: WO2014/080939
PCT Pub. Date: May 30, 2014

(65) Prior Publication Data
US 2015/0291635 A1    Oct. 15, 2015

(30) Foreign Application Priority Data

Nov. 20, 2012 (JP) .................. 2012-254712
Jun. 21, 2013 (JP) .................. 2013-130982

(51) Int. Cl.
*C07F 9/50* (2006.01)
*C07F 7/28* (2006.01)
(Continued)

(52) U.S. Cl.
CPC .............. *C07F 7/28* (2013.01); *B01J 8/02* (2013.01); *B01J 31/1805* (2013.01);
(Continued)

(58) Field of Classification Search
None
See application file for complete search history.

(56) References Cited

U.S. PATENT DOCUMENTS 5,541,349 A * 7/1996 Wilson ................ C07F 7/00
                                                           502/117
2008/0139822 A1* 6/2008 Tanaka ............... C07B 53/00
                                                           548/414

(Continued)

FOREIGN PATENT DOCUMENTS

JP    2004-83534     3/2004
JP    2004-115401    4/2004

OTHER PUBLICATIONS

International Search Report, International Patent Application No. PCT/JP2013/081276, dated Feb. 25, 2014.
(Continued)

*Primary Examiner* — Wayne Langel
(74) *Attorney, Agent, or Firm* — Casimir Jones, SC

(57) ABSTRACT

A novel complex capable of fixing dinitrogen and use thereof are provided. A complex represented by formula (1A) or (1B) or a cationic or anionic complex from the complex:

[Chem. 1]

(1A)

(Continued)

(1B)

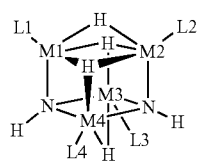

wherein M1 to M4 (M1 to M3 in the case of formula (1A)) are each independently Ti, Zr, Hf, V, Nb, Ta, Cr, Mo, or W, and L1 to L4 (L1 to L3 in the case of formula (1A)) are each independently a ligand selected from among a ligand (Cp) including a substituted or unsubstituted cyclopentadienyl derivative, a diphenylamine ligand, a diphenylphosphine ligand, and a carboimideamide ligand.

16 Claims, 10 Drawing Sheets

(51) Int. Cl.
| | | |
|---|---|---|
| *C07F 7/00* | (2006.01) | |
| *C07F 9/00* | (2006.01) | |
| *C07F 11/00* | (2006.01) | |
| *C01C 1/04* | (2006.01) | |
| *B01J 8/02* | (2006.01) | |
| *C07F 17/00* | (2006.01) | |
| *B01J 31/18* | (2006.01) | |
| *B01J 31/22* | (2006.01) | |
| *B01J 31/24* | (2006.01) | |

(52) U.S. Cl.
CPC ....... *B01J 31/2295* (2013.01); *B01J 31/2404* (2013.01); *C01C 1/0411* (2013.01); *C07F 7/006* (2013.01); *C07F 9/5045* (2013.01); *C07F 17/00* (2013.01); *B01J 2208/00805* (2013.01); *B01J 2231/62* (2013.01); *B01J 2531/0222* (2013.01); *B01J 2531/46* (2013.01); *C07F 7/00* (2013.01); *C07F 9/00* (2013.01); *C07F 9/5022* (2013.01); *C07F 11/005* (2013.01); *Y02P 20/52* (2015.11)

(56) References Cited

U.S. PATENT DOCUMENTS

| | | | | |
|---|---|---|---|---|
| 2010/0099875 A1* | 4/2010 | Stephan | ............... | B01J 31/2404 546/21 |
| 2011/0089410 A1* | 4/2011 | Stoessel | .................. | C07F 1/005 257/40 |
| 2014/0186253 A1* | 7/2014 | Kitagawa | ............... | C08G 79/00 423/362 |

OTHER PUBLICATIONS

Shima T. et al. "Dinitrogen Cleavage and Hydrogenation by a Trinuclear Titanium Polyhydride Complex," Science, vol. 340, No. 6140, 2013, p. 1549-1552.
Brintzinger H. "Formation of Ammonia by Insertion of Molecular Nitrogen into Metal-Hydride Bonds. II. Di-μ-imino-bis(dicyclopentadienyltitanium(III)) as a Product of the Reaction between Di-μ-hydrido-bis(dicyclopentadienyltitanium (III)) and Molecular Nitrogen," J. Am. Chem. Soc., 1966, 88 (18), pp. 4307-4308.
Dziegielewski J.O. et al. Photoreduction of moleclar nitrogen using the complex [ReH5(dppe) (PPh3)] Polyhedron vol. 16, No. 12, 1997, pp. 1979-1981.
Dziegielewski J.O. et al. "The Cyclic Fixation and Reduction of Molecular Nitrogen With [WH4 (Ph2PCH2CH2PPh2) 2] in y-Irradiated Solutions," Polyhedron vol. 10, No. 23/24, 1991, pp. 2827-2832.
Dziegielewski J.O. "Application of the Molybdenum(IV) Hydride Complexes in Cyclohexane Solutions to the Radiation-Catalytic Reduction of Molecular Nitrogen," Polyhedron vol. 9, No. 5, 1990, pp. 645-651.
Shima T. et al. "Tetra-, Penta-, and Hexanuclear Yttrium Hydride Clusters from Half-Sandwich Bis(aminobenzyl) Complexes Containing Various Cyclopentadienyl Ligands," Organometallics vol. 30, No. 9, 2011, pp. 2513-2524.
Martinez-Espada N. et al. "Cyclopentadienyl and Alkynyl Copper(I) Derivatives with the [{Ti (r5-CSMes) (p-NH) }3 (p3-N)]Metalloligand," Organometallics vol. 29, No. 24, 2010, pp. 6733, scheme 1, compound 1.
Kawaguchi H. et al. "Dinitrogen cleavage by a diniobium tetrahydride complex: formation of a nitride and its conversion into imide species," Angew Chem Int Ed Engl. 2007;46(46):8778-81.
Fryzuk M.D. et al. "Transformation of Coordinated Dinitrogen by Reaction with Dihydrogen and Primary Silanes," Science, 1997, 275, 1445.
Nishibayashi Y. et al. "A molybdenum complex bearing PNP-type pincer ligands leads to the catalytic reduction of dinitrogen into ammonia," Nature Chemistry, 2011, 2, 120-125.
Schrock R. R. et al. "Catalytic Reduction of Dinitrogen to Ammonia at a Single Molybdenum Center" Science Jul. 4, 2003, vol. 301, pp. 76.
European Search Report, European Patent Application No. 13856069.3, dated Jun. 15, 2016, 9 pages.
Carbo et al. "Lewis Base Behavior of Bridging Nitrido Ligands of Titanium Polynuclear Complexes" Chemistry—A European Journal, vol. 15, No. 43, Nov. 2, 2009, pp. 11619-11631.
Pool et al. "Hydrogenation and cleavage of dinitrogen to ammonia with a zirconium complex" Nature, vol. 427, No. 6974, Feb. 5, 2004, pp. 527-530.

\* cited by examiner

COMPLEX AND USE OF SAME

TECHNICAL FIELD

The present invention relates to a novel hydrido complex capable of fixing dinitrogen, a method for synthesizing the hydrido complex, and use of the hydrido complex.

BACKGROUND ART

A technology for fixing dinitrogen and using them is extremely important in industry, including the agricultural sector. In nature, the fixation of dinitrogen is known for example as the fixation of dinitrogen by root nodule bacteria. Industrially, however, the fixation of dinitrogen is performed exclusively by the Haber-Bosch process.

CITATION LIST

Non-Patent Literature

Non-Patent Literature 1
R. R. Schrock, *Science,* 2003, 301, 76.
Non-Patent Literature 2
Nishibayashi, *Nature Chem.,* 2010, 2, 120.
Non-Patent Literature 3
M. D. Fryzuk, et al., *Science,* 1997, 275, 1445.
Non-Patent Literature 4
H. Kawaguchi et al., *Angew. Chem. Int. Ed.,* 2007, 46, 8778.

SUMMARY OF INVENTION

Technical Problem

However, the Haber-Bosch process is a technique that can only be efficiently implemented in a very high-temperature and high-pressure environment. Therefore, there has been a desperate need for a technique for performing dinitrogen fixation in a milder environment.

It should be noted that metal complexes (Non-patent Literatures 1 and 2 etc.) or hydrido complexes (Non-patent Literatures 3 and 4 etc.) capable of fixing dinitrogen have been reported. However, none of them fixes dinitrogen in a form that can be easily taken as ammonia from the complex. For industrial applications, there has been a desperate need for a further novel proposal.

The present invention has been made in view of the problems described above, and it is an object of the present invention to provide a novel hydrido complex that fixes dinitrogen in a relatively mild environment, a method for synthesizing the hydrido complex, and use of the hydrido complex.

Solution to Problem

In order to attain the object, the present invention provides any one of the following:

(1) A complex represented by formula (1A) or (1B) or a cationic or anionic complex from the complex:

[Chem. 1]

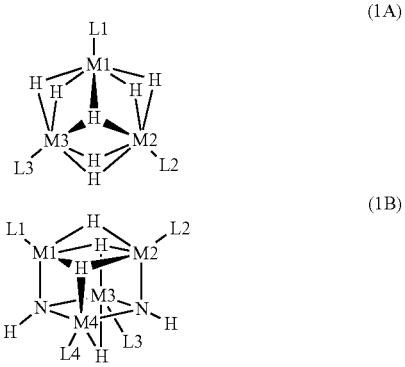

wherein M1 to M4 (M1 to M3 in the case of formula (1A)) are each independently Ti, Zr, Hf, V, Nb, Ta, Cr, Mo, or W, and L1 to L4 (L1 to L3 in the case of formula (1A)) are each independently a ligand selected from among a ligand (Cp) including a substituted or unsubstituted cyclopentadienyl derivative, a diphenylamine ligand, a diphenylphosphine ligand, and a carboimideamide ligand.

(2) The complex as set forth in (1), wherein L1 to L4 (L1 to L3 in the case of formula (1A)) of formulas (1A) and (1B) are identical ligands each of which is represented by formula (2):

[Chem. 2]

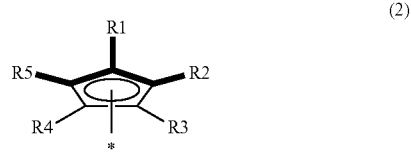

wherein R1 to R5 are each independently a hydrogen atom that binds to a carbon atom constituting the skeleton of the cyclopentadienyl ring; a C1-C20 hydrocarbyl group; or a substituted metalloid group in which a C1-C20 hydrocarbyl group, an amide group, a phosphide group, and/or an alkoxide group has/have been substituted, ·X· is a bond with M1 to M4 (M1 to M3 in the case of formula (1A)), and two to five of R1 to R5 are the hydrocarbyl group or substituted metalloid group, and wherein one of the carbon atoms constituting the skeleton of the cyclopentadienyl ring may be substituted by a 14th-group atom (excluding a carbon atom and a lead atom) or a 15th-group atom.

(3) The complex as set forth in (2), wherein, in formula (2), all of R1 to R5 are methyl groups, or four of R1 to R5 are methyl groups and the other one of R1 to R5 is a trialkylsilyl group.

(4) The complex as set forth in any one of (1) to (3), wherein each of M1 to M4 (M1 to M3 in the case of formula (1A)) of formulas (1A) and (1B) is Ti.

(5) A complex as set forth in any one of (1) to (4), the complex being represented by formula (1A).

(6) A complex having nitrogen atoms incorporated therein by bringing a complex as set forth in any one of (1) to (5) and nitrogen molecules into contact with each other.

(7) The complex as set forth in (6), the complex being a complex represented by formula (3) or a cationic or anionic complex from the complex:

[Chem. 3]

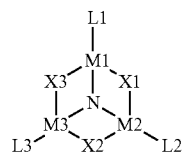
(3)

wherein M1 to M3 and L1 to L3 are identical to those of formula (1A), X1 to X3 are each —H— or —N(H)—, and at least one of X1 to X3 is —N(H)—, and in one or more —N(H)—'s, H may be substituted by a boryl group, a silyl group, or an alkyl group.

(8) A complex represented by formula (3') or a cationic or anionic complex from the complex:

[Chem. 4]

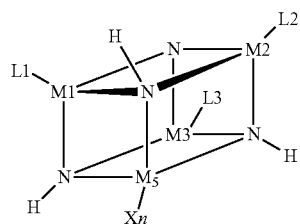
(3')

wherein M1 to M3 are each independently Ti, Zr, Hf, V, Nb, Ta, Cr, Mo, or W, L1 to L3 are each independently a ligand selected from among a ligand (Cp) including a substituted or unsubstituted cyclopentadienyl derivative, a diphenylamine ligand, a diphenylphosphine ligand, and a carboimideamide ligand, M5 is Cu, Zn, Sc, or Y, X is F, Cl, Br, I, or —OSO$_2$CF$_3$, and n (which indicates the number of X's) is an integer represented by p-3 (where p is the coordination number of M5).

(9) A method for synthesizing ammonia, comprising the step of bringing hydrogen molecules and nitrogen molecules into contact with a complex as set forth in any one of (1) to (8) or brining hydrogen molecules into contact with a complex as set forth in claim (6) or (7).

(10) A fixed bed for use in ammonia synthesis, comprising a complex as set forth in any one of (1) to (8), the complex being fixed.

Advantageous Effects of Invention

The present invention can provide a novel hydrido complex that fixes dinitrogen in a relatively mild environment, a method for synthesizing the hydrido complex, and use of the hydrido complex.

DESCRIPTION OF EMBODIMENTS

Figure 1:
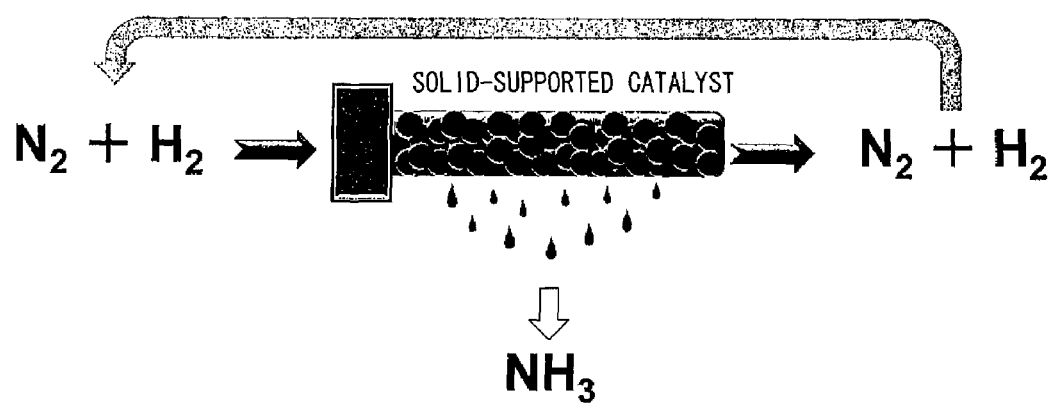
FIG. 1 schematically shows an example of a method for synthesizing ammonia that can be carried out with use of a metal polyhydrido complex according to the present invention.

[1. Complex]
(Complex According to the Present Invention)

An example of a complex according to the present invention is a hydrido complex represented by formula (1A) or formula (1B):

[Chem. 5]

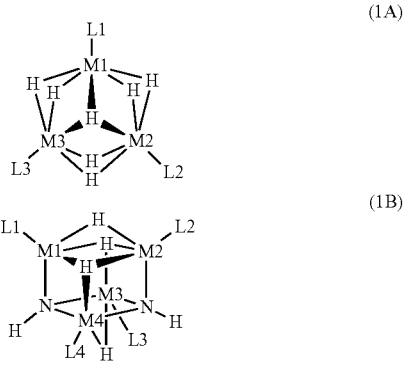

In formula (1A), M1 to M3 are each independently Ti (titanium atom), Zr, (zirconium atom), Hf (hafnium atom), V (vanadium atom), Nb (niobium atom), Ta (tantalum atom), Cr (chromium atom), Mo (molybdenum atom), or W (tungsten atom), preferably each independently Ti, Zr, or Hf. Preferably, all of M1 to M3 are identical atoms. More preferably, all of M1 to M3 are Ti. Similarly, in formula (1B), M1 to M4 are each independently Ti, Zr, Hf, V, Nb, Ta, Cr, Mo, or W, preferably each independently Ti, Zr, or Hf. Preferably, all of M1 to M4 are identical atoms. More preferably, all of M1 to M4 are Ti.

In formula (1A), L1 to L3 are each independently is a ligand selected from among a ligand (referred to as "Cp ligand") including a substituted or unsubstituted cyclopentadienyl derivative, a diphenylamine ligand, a diphenylphosphine ligand, and a carboimideamide ligand. Preferably, all of L1 to L3 are identical ligands. More preferably, all of L1 to L3 are identical Cp ligands. Similarly, in formula (1B), L1 to L4 are each independently is a ligand selected from among a substituted or unsubstituted Cp ligand, a diphenylamine ligand, a diphenylphosphine ligand, and a carboimideamide ligand. Preferably, all of L1 to L4 are identical ligands. More preferably, all of L1 to L4 are identical Cp ligands.

In the present invention, the Cp ligand is pi-bonded to the central metal M. The Cp ligand is for example a non-bridging ligand. The term "non-bridging ligand" here means a ligand whose cyclopentadienyl derivative is pi-bonded to the central metal and which does not have a coordinating atom or a coordinating group other than the cyclopentadienyl derivative. Alternatively, the Cp ligand is for example a bridging ligand. The term "bridging ligand" here means a ligand which further includes a coordinating atom or a coordinating group in addition to the cyclopentadienyl derivative. The Cp ligand is preferably a non-bridging ligand.

The substituted or unsubstituted cyclopentadienyl derivative of the Cp ligand is one selected from the group consisting of a substituted or unsubstituted cyclopentadienyl ring, a substituted or unsubstituted fluorenyl ring, a substituted or unsubstituted octahydro fluorenyl ring, a substituted or unsubstituted indenyl ring, and a substituted or unsubstituted tetrahydroindenyl ring. Among them, the most preferred cyclopentadienyl derivative is a cyclopentadienyl ring having a substituent(s).

The cyclopentadienyl ring is represented by the composition formula: $C_5H_{5-X}R_X$. In this composition formula, X represents an integer of 0 to 5. Each R is independently a hydrocarbyl group; a substituted hydrocarbyl group; or a substituted metalloid group in which a hydrocarbyl group, an amide group, a phosphide group, and/or an alkoxide group has/have been substituted. It should be noted that one of C in the composition formula may be substituted by a 14th-group atom (excluding a carbon atom and a lead atom) or a 15th-group atom.

The hydrocarbyl group is preferably a C1-C20 hydrocarbyl group, more preferably a C1-C20 (preferably C1-C10, more preferably C1-C6) alkyl group, phenyl group, benzyl group, etc., most preferably a methyl group.

Further, an example of a hydrocarbyl group having a substituent (the substituted hydrocarbyl group) is a hydrocarbyl group at least one of the hydrogen atoms of which has been substituted by a halogen atom, am amide group, a phosphide group, an alkoxy group, an aryloxy group, or the like.

Further, examples of the metalloid in the substituted metalloid group include germyl (Ge), stannyl (Sn), silyl (Si), etc. Further, the number of substitutions of substituents having substituted in the metalloid group is determined by the type of metalloid (e.g. in the case of a silyl group, the number of substitutions of hydrocarbyl groups (substituents) is 3). It should be noted that the carbon number of a hydrocarbyl group as a substituent in the substituted metalloid group is preferably in the range of 1 to 20.

It should be noted that at least one of the R groups of the cyclopentadienyl ring is a substituted metalloid group (preferably a silyl group) in which a hydrocarbyl group has been substituted, more preferably a trimethylsilyl group.

A preferred example of the cyclopentadienyl ring is represented by formula (2):

[Chem. 6]

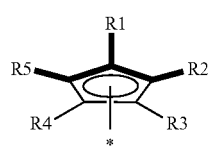

(2)

In formula (2), R1 to R5 are each independently a hydrogen atom that binds to a carbon atom constituting the skeleton of the cyclopentadienyl ring; a C1-C20 hydrocarbyl group; or a substituted metalloid group in which a C1-C20 hydrocarbyl group, an amide group, a phosphide group, and/or an alkoxide group has/have been substituted, ·X· is a bond with M1 to M3 in formula (1A) or a bond with M1 to M4 in formula (1B), and two to five of R1 to R5 are the hydrocarbyl group or substituted metalloid group. Further, one of the carbon atoms constituting the skeleton of the cyclopentadienyl ring represented by formula (2) may be substituted by a 14th-group atom (excluding a carbon atom and a lead atom) or a 15th-group atom. It should be noted that it is preferable that L1 to L3 in formula (1A) or L1 to L4 in formula (1B) be identical ligands represented by formula (2).

The following are examples of the cyclopentadienyl ring represented by formula (2):

[Chem. 7]

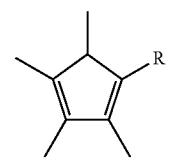

(3-1)

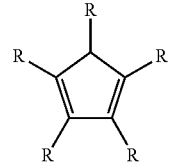

(3-2)

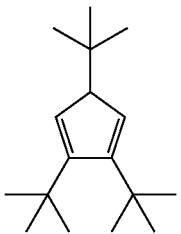

(3-3)

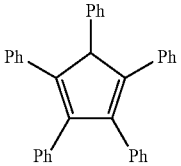

(3-4)

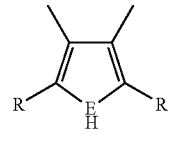

(3-5)

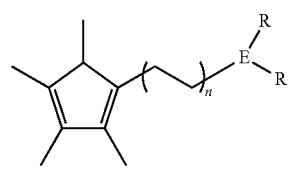

(3-6)

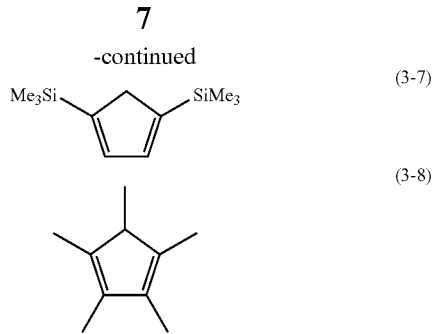

(3-7)

(3-8)

In formulas (3-1), (3-2), and (3-5), each R is independently a substituted metalloid group in which a C1-C20 hydrocarbyl group, an amide group, a phosphide group, and/or an alkoxide group has/have been substituted (preferably a substituted metalloid group in which a C1-C20 hydrocarbyl group has been substituted). A specific example of this metalloid group is any one of those represented by formula (4) below. In formula (4), each R' is independently a C1-C8 hydrocarbyl group, preferably a C1-C6 hydrocarbyl group, more preferably a C1-C4 hydrocarbyl group (preferably a chain alkyl group).

[Chem. 8]

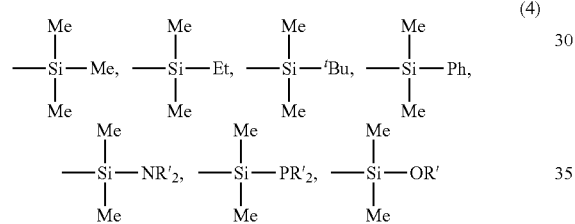

(4)

In formula (3-5), E is N (nitrogen atom) or P (phosphorus atom).

Further, in formula (3-6), each R is independently a C1-C20 hydrocarbyl group (preferably a C1-C6 chain alkyl group); or a substituted metalloid group in which a C1-C20 hydrocarbyl group, an amide group, a phosphide group, and/or an alkoxide group has/have been substituted (preferably a substituted metalloid group in which a C1-C20 hydrocarbyl group has been substituted). A specific example of this metalloid group is any one of those represented by formula (4) above. Furthermore, in formula (3-6), n is an integer of 1 or larger to 5 or smaller, and E is a hetero atom such as N (nitrogen atom), P (phosphorous atom), or As (arsenic atom), preferably N or P.

Further, an example of the cyclopentadienyl ring represented by formula (2) is one (which is equivalent to formula (3-8) in which, in formula (2), all of R1 to R5 are methyl groups (which is equivalent to formula (3-8) or one (which is equivalent to formula (3-1)) in which, in formula (2), four of R1 to R5 are methyl groups and the other one of R1 to R5 is a trialkylsilyl group having a C1-C6 alkyl group.

As the Cp ligand, the substituted or unsubstituted fluorenyl ring is represented by the composition formula: $C_{13}H_{9-X}R_X$ (where X is an integer of 0 to 9, and R is either a C1-C20 hydrocarbyl group that may have a substituent or a substituted metalloid group and is similar to the R of the aforementioned cyclopentadienyl ring: $C_5H_{5-X}R_X$). Alternatively, as the Cp ligand, the substituted or unsubstituted octahydro fluorenyl ring is represented, for example, by the composition formula: $C_{13}H_{17-X}R_X$ (where X is an integer of 0 to 17, and R is either a C1-C20 hydrocarbyl group that may have a substituent or a substituted metalloid group and is similar to the R of the aforementioned cyclopentadienyl ring: $C_5H_{5-X}R_X$).

Preferred examples of the fluorenyl ring are represented by the following formulas:

[Chem. 9]

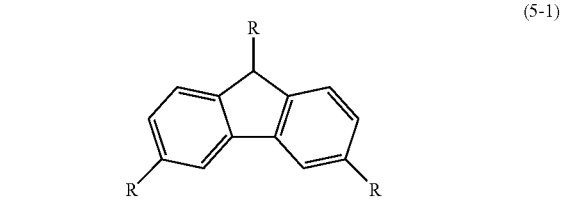

(5-1)

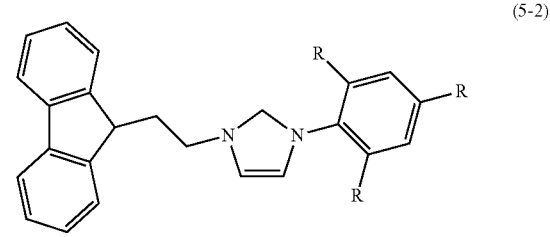

(5-2)

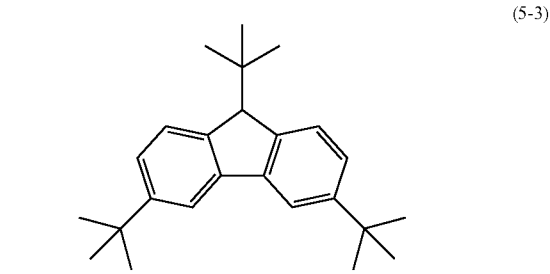

(5-3)

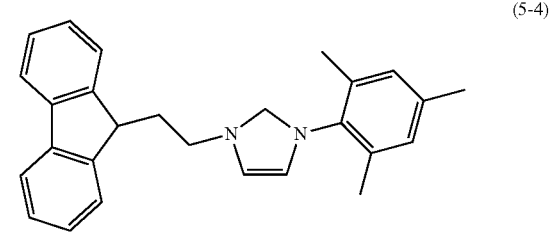

(5-4)

In formulas (5-1) and (5-2), each R is independently a C1-C20, preferably C1-C6, hydrocarbyl group or a substituted metalloid group. A specific example of this metalloid group is any one of those represented by formula (4) above. Formulas (5-3) and (5-4) are equivalent to specific examples of compounds represented by formulas (5-1) and (5-2), respectively.

The Cp ligand may alternatively be a substituted or unsubstituted indenyl ring (composition formula: $C_9H_{7-X}R_X$, where X is an integer of 0 to 7), tetrahydroindenyl ring (composition formula: $C_9H_{11-X}R_X$, where X is an integer of 0 to 11), or the like. In these formulas, R is similar to the R of the aforementioned cyclopentadienyl ring.

A preferred example of the indenyl ring is represented by formula (6):

[Chem. 10]

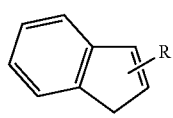
(6)

In formula (6), each R is independently a C1-C20, preferably C1-C6, hydrocarbyl group or a substituted metalloid group. A specific example of this metalloid group is any one of those represented by formula (4) above.

In the present invention, the diphenylamine ligand is a ligand having a diphenylamine skeleton (—N(Ph)$_2$) in which two phenyl groups are bonded to a nitrogen atom. Any hydrogen atom on each of the phenyl groups may be substituted, for example, by a C1-C20 hydrocarbyl group, a metalloid group in which a C1-C20 hydrocarbyl group has been substituted, or a substituent such as a —PR$_2$ group, a —SR group, or a —OR group. In the —PR$_2$ group, the —SR group, and the —OR group, each R is independently a C1-C20, preferably C1-C6, hydrocarbyl group or a metalloid group in which such a hydrocarbyl group has been substituted. It should be noted that it is preferable that the two R groups of the —PR$_2$ group be identical to each other. A preferred example of the diphenylamine ligand is represented by formula (7):

[Chem. 11]

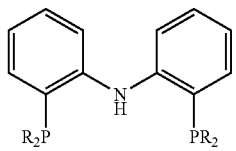
(7)

In formula (7), each R is independently a C1-C20, preferably C1-C6, hydrocarbyl group or a substituted metalloid group. A specific example of this metalloid group is any one of those represented by formula (4) above. In a case where R is a hydrocarbyl group, it is preferable that the hydrocarbyl group be an alkyl group or an aryl group. In formula (7), it is preferable that the four R groups be identical groups.

In the present invention, the diphenylphosphine ligand is a ligand having a diphenylphosphine skeleton (—P(Ph)$_2$) in which two phenyl groups are bonded to a phosphorous atom. Any hydrogen atom on each of the phenyl groups may be substituted, for example, by a C1-C20 hydrocarbyl group, a metalloid group in which a C1-C20 hydrocarbyl group has been substituted, or a substituent such as a —SR group or a —OR group. In the —SR group and the —OR group, each R is independently a C1-C20, preferably C1-C6, hydrocarbyl group or a metalloid group in which such a hydrocarbyl group has been substituted.

A preferred example of the diphenylphosphine ligand is represented by formula (8):

[Chem. 12]

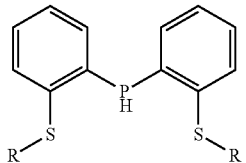
(8)

In formula (8), each R is independently a C1-C20, preferably C1-C6, hydrocarbyl group or a substituted metalloid group. A specific example of this metalloid group is any one of those represented by formula (4) above. In a case where R is a hydrocarbyl group, it is preferable that the hydrocarbyl group be an alkyl group or an aryl group. In formula (8), it is preferable that the two R groups be identical groups.

In the present invention, the carboimideamide ligand is a ligand having a structure (—N=C—NH— structure) represented by formula (9):

[Chem. 13]

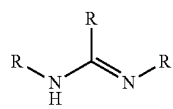
(9)

In formula (9), each R may be independently any group, but in a preferred carboimideamide ligand, each R is independently a C1-C20, preferably C1-C6, hydrocarbyl group or a substituted metalloid group. A specific example of this metalloid group is any one of those represented by formula (4) above. In a case where R is a hydrocarbyl group, it is preferable that the hydrocarbyl group be an alkyl group or an aryl group. More specific examples of the carboimideamide ligand include N1,N1-diphenylbenzene carboimideamide etc.

It should be noted that the hydrido complex represented by formula (1A) and the hydrido complex represented by formula (1B) may each be not only a neutral complex, but also a cationic or anionic complex that is obtained from the neutral complex. Specific examples of complexes according to the present invention encompass: a cationic complex, such as [{(C$_5$Me$_4$SiMe$_3$)Ti}$_3$(μ-H)$_6$][B(C$_6$F$_5$)$_4$] or [{(C$_5$Me$_4$SiMe$_3$)Ti}$_3$(μ-H)$_5$H][{B(C$_6$F$_5$)$_4$}$_2$], which is obtained from a neutral complex [{(C$_5$Me$_4$SiMe$_3$)Ti}$_3$(μ$_3$-H)(μ$_2$-H)$_6$]; and an anionic complex, such as Li[{(C$_5$Me$_4$SiMe$_3$)Ti}$_3$(μ-H)$_8$], which is obtained from [{(C$_5$Me$_4$SiMe$_3$)Ti}$_3$(μ$_3$-H)(μ$_2$-H)$_6$].

(Method for Synthesizing a Complex According to the Present Invention)

The hydrido complex represented by formula (1A) may be synthesized by any method. For example, the hydrido complex represented by formula (1A) may be synthesized by bringing a compound represented by formula (10) and hydrogen molecules into contact with each other.

[Chem. 14]

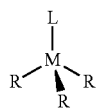
(10)

It should be noted that M in formula (10) is identical to M1 to M3 in formula (1A), and L in formula (10) is identical to L1 to L3 in formula (1A). That is, use of only one type of compound represented by formula (10) gives a complex represented by formula (1A) in which M1 to M3 are identical and L1 to L3 are identical.

Further, in formula (10), each R is independently a monoanionic ligand. More specific examples of R include, but are not limited to, monoanionic ligands such as hydrido, halide, a substituted or unsubstituted C1-C20 hydrocarbyl group, an alkoxy group or aryloxy group, and an amide group or a phosphino group. Among these, each R is preferably independently a C1-C20 hydrocarbyl group that may have a substituent, particularly preferably a trimethylsilyl group.

Examples of the halide include chloride, bromide, fluoride, and iodide.

Preferred examples of the C1-C20 hydrocarbyl group include: alkyl groups such as a methyl group, an ethyl group, a propyl group, a butyl group, an amyl group, an isoamyl group, a hexyl group, an isobutyl group, a heptyl group, an octyl group, a nonyl group, a decyl group, a cetyl group, and a 2-ethylhexyl group; and unsubstituted hydrocarbyl groups such as a phenyl group and a benzyl group. Other possible examples include substituted hydrocarbyl groups such as a substituted benzyl group, a trialkylsilylmethyl group, and a bis(trialkylsilyl) group. Preferred examples of the hydrocarbyl group include a methyl group, an ethyl group, a phenyl group, a substituted or unsubstituted benzyl group, and a trialkylsilylmethyl group, and more preferred examples include a trimethylsilylmethyl group.

Preferred examples of the alkoxy group or aryloxy group include a methoxy group, a substituted or unsubstituted phenoxy group, and the like.

Preferred examples of the amide group include a dimethylamide group, a diethylamide group, a methylethylamide group, a di-t-butylamide group, a diisopropylamide group, a substituted or unsubstituted diphenylamide group, and the like.

Preferred examples of the phosphino group include a diphenyl phosphino group, a dicyclohexyl phosphino group, a diethyl phosphino group, a dimethyl phosphino group, and the like.

Preferred examples of alkylidene include methylidene, ethylidene, propylidene, and the like.

Further, R groups may bind to each other, or may be combined to form a dianionic ligand (dianion ligand) or a trianionic ligand (trianion ligand). Examples of the dianionic ligand include alkylidene, diene, a cyclo-metalated hydrocarbyl group, a bidentate chelate ligand, and the like.

The compound represented by formula (10) and hydrogen molecules can be brought into contact with each other preferably in a solvent in which the compound represented by formula (10) can dissolve. The type of solvent needs only be selected according to the type of compound represented by formula (10). Examples of the solvent include hexane, pentane, heptane, a mixed solvent obtained by mixing two or more of these solvents, and the like. Further, the solvent is not limited to a particular temperature during the contact, and the temperature can be selected according to the type of solvent. For example, the temperature falls within the range of 25° C. to 80° C., preferably the range of 40° C. to 60° C. Further, for the purpose of increasing the amount of hydrogen molecules that are supplied into the solvent, it is preferable that the hydrogen molecules (gas) be supplied as a pressurized gas. For example, the hydrogen molecules are supplied while being kept at a pressure that is higher than normal pressure but equal to or lower than a pressure of 5 atmospheres (atm).

The duration of contact (reaction) between the compound represented by formula (10) and hydrogen molecules is not limited to a particular length of time. For example, the duration falls within the range of 4 hours to 24 hours, preferably the range of 12 hours to 24 hours. Further, the molar ratio between the compound represented by formula (10) and hydrogen molecules for use in contact needs only be determined in consideration of the reaction equivalents thereof, and is not limited to a particular molar ratio.

It is preferable that a reaction product obtained through the reaction between the compound represented by formula (10) and hydrogen molecules be collected as a precipitate that is obtained, for example, by performing washing or the like of the product, then adding the product into a first crystallization solvent for crystallization to collect a solution phase, and then replacing the solvent of the solution phase thus collected with a second crystallization solvent for recrystallization. Examples of the first crystallization solvent include THF and the like. Further, examples of the second crystallization solvent include hexane and the like.

It should be noted that a cationic complex from the hydrido complex represented by formula (1A) can be synthesized, for example, from a neutral hydrido complex and a promoter such as $[Ph_3C][B(C_6F_5)_4]$, $B(C_6F_5)_3$, or methylaluminoxane (MAO). Furthermore, an anionic complex from the hydrido complex represented by formula (1A) can be synthesized, for example, by adding to a neutral hydrido complex any of the following: a combination of R—Li (organic lithium compound) such as $Me_3SiCH_2Li$ and $H_2$; a combination of a Grignard reagent such as RMgBr and $H_2$; and a combination of NaH or KH and $H_2$. It should be noted here that R is for example an alkyl group or another hydrocarbon group. Further, the elements constituting the combination may be added to the neutral hydrido complex under any condition (e.g. in any order.

It should be noted that the descriptions in the Examples below, too, are referred to regarding the method for synthesizing the hydrido complex represented by formula (1A).

Further, the hydrido complex represented by formula (1B) may be synthesized by any method. For example, the hydrido complex represented by formula (1B) may be synthesized by bringing the aforementioned compound represented by formula (10), hydrogen molecules, and nitrogen molecules into contact with one another.

It should be noted that M in formula (10) is identical to M1 to M4 in formula (1B), and L in formula (10) is identical to L1 to L4 in formula (1B). That is, use of only one type of compound represented by formula (10) gives a complex represented by formula (1B) in which M1 to M4 are identical and L1 to L4 are identical. Further, a cationic or anionic complex from the hydrido complex represented by formula (1B) can be synthesized according to the method for synthesizing a cationic or anionic complex from the hydrido complex represented by formula (1A).

[2. Nitrogen-Fixed Complex (Nitrogen Fixation Complex)]

The present invention also provides a complex (hereinafter referred to as "nitrogen fixation complex") formed by the incorporation of nitrogen atoms. This complex is obtained by bringing at least one type of complex and nitrogen molecules into contact with each other. The at least one type of complex is selected from the group consisting of a hydrido complex represented by formula (1A), a hydrido complex represented by formula (1B), and a cationic or anionic complex from any of these complexes.

A preferred example of the nitrogen fixation complex is a complex represented by formula (3) or a cationic or anionic complex from the complex:

[Chem. 15]

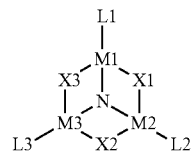

(3)

In formula (3), M1 to M3 and L1 to L3 are identical to those of formula (1A), X1 to X3 are each —H— or —N(H)—, and at least one (preferably two or three) of X1 to X3 is —N(H)—. It should be noted that the —'s of X1 to X3 are binding arms to M1 to M3.

In the complex represented by formula (3) or a cationic or anionic complex from the complex, nitrogen atoms are incorporated in such a manner that the NN triple bond in the nitrogen molecule is dissociated and a N—H bond is formed. This makes it easy to release the incorporated nitrogen atoms under relatively mild conditions as will be described later.

Further, in the complex represented by formula (3), the H of at least one of X1 to X3, which are —N(H)—, may be substituted by a substituent such as a boryl group (e.g. a pinacol boryl group), a silyl group, or an alkyl group, so that a complex having a boron bond(s), a silicon bond(s), or a carbon bond(s) may be formed. The addition of various functional groups to nitrogen allows nitrogen to be used, for example, for the synthesis of a nitrogen-containing organic compound.

For example, in a case where at least one of the —N(H)—'s of the complex represented by formula (3) is boronated with pinacol borane ($HB_{pin}$), pinacol borane ($HB_{pin}$) (36 mg, 0.3 mmol) is brought into reaction in the time range of 30 minutes to 12 hours, in the temperature range of 20° C. to 80° C., and in the presence of $C_6D_6$.

It should be noted that a method for synthesizing the complex represented by formula (3) or a cationic or anionic complex from the complex will be described in section [3. Method for Synthesizing Ammonia] below.

Another example of the nitrogen fixation complex is a complex that is obtained, for example, by bringing the complex represented by formula (3) or a cationic or anionic complex from the complex into contact with a Lewis acid (which will be defined later) represented by formula $M5X_n$. A particularly preferred example is a complex represented by formula (3') or a cationic or anionic complex from the complex. The complex represented by formula (3') or a cationic or anionic complex from the complex is obtained, for example, by bringing a complex represented by formula (3) in which all three of X1 to X3 are —N(H)—'s or a cationic or anionic complex from the complex into contact with the Lewis acid represented by formula $M5X_n$.

[Chem. 16]

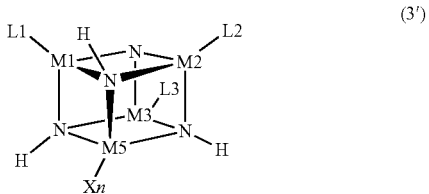

(3')

In formula (3'), M1 to M3 are each independently Ti, Zr, Hf, V, Nb, Ta, Cr, Mo, or W, and L1 to L3 are each independently a ligand selected from among a ligand (Cp) including a substituted or unsubstituted cyclopentadienyl derivative, a diphenylamine ligand, a diphenylphosphine ligand, and a carboimideamide ligand. The definition of these ligands is the same as that of the complex represented by formula (3). It should be noted that in a case where the complex of formula (3') is obtained by bringing the complex represented by formula (3) or a cationic or anionic complex from the complex into contact with the Lewis acid represented by formula $M5X_n$, M1 to M3 and L1 to L3 in formula (3') are identical to those of formula (3). M 5 is for example Cu (copper), Zn (zinc), Sc (scandium), or Y (yttrium), X is F, Cl, Br, I, or —$OSO_2CF_3$, and n (which indicates the number of X's) is an integer represented by p-3 (where p is the coordination number of M5; for example, p is 4 in a case where M5 is Cu, p is 5 in a case where M5 is Zn, and p is 6 in a case where M5 is Sc). It is preferable that M5 be selected from among Cu, Zn, and Sc. Further, for example, X is Cl.

It should be noted that a method for synthesizing the complex represented by formula (3') or a cationic or anionic complex from the complex will be described in section [3. Method for Synthesizing Ammonia] below.

[3. Method for Synthesizing Ammonia]

The present invention provides a method for synthesizing ammonia with use of a complex represented by formula (1A), a complex represented by formula (1B), a cationic or anionic complex from any of these complexes, or the nitrogen fixation complex described above.

An example of synthesis of ammonia with use of a complex represented by formula (1A) include a dinitrogen fixing/converting step of bringing hydrogen molecules and nitrogen molecules into contact with the complex. The dinitrogen fixing/converting step may be performed by a process (A) of bringing nitrogen molecules into contact with the complex represented by formula (1A) for dinitrogen fixation and then further bringing hydrogen molecules into contact with the complex or a process (B) of bringing hydrogen molecules and nitrogen molecules into contact with the complex in a simultaneous parallel manner.

In the synthesis of ammonia by the process (A), first, a nitrogen fixation complex represented by formula (3) is formed by bringing nitrogen molecules into contact with the complex represented by formula (1A). Then, presumably, ammonia is synthesized by hydrogen molecules being brought into contact with the nitrogen fixation complex represented by formula (3). Further, presumably, the nitrogen fixation complex represented by formula (3) returns to the complex represented by formula (1A) when the nitrogen atoms having been fixed is released along with the synthesis of ammonia. This makes it possible to continuously synthesize ammonia by continuously bringing hydrogen molecules and nitrogen molecules into contact with the complex represented by formula (1A) through repeated application of the process (A) to the complex.

In the process (A), nitrogen molecules may be brought into contact with the complex represented by formula (1A) under any conditions. For example, nitrogen molecules may be brought into contact with the complex represented by formula (1A) in the temperature range of −30° C. to 200° C. and at a pressure (partial pressure in the case of a mixture gas) of nitrogen molecules (nitrogen gas) in the range of 1 atm to 100 atm. The duration of contact (reaction) is not limited to a particular length of time. For example, the duration falls within the range of 1 hour to 24 hours. Nitrogen molecules need only be brought into contact with the complex represented by formula (1A) as simple nitrogen molecules or as a component of a mixture gas. The mixture gas may be one that contains hydrogen molecules and nitrogen molecules, but is preferably one that contains more nitrogen molecules in number of moles. In a case where the synthesis of a nitrogen fixation complex represented by formula (3) in which one of X1 to X3 is —N(H)—, the synthesis of a nitrogen fixation complex represented by formula (3) in which two of X1 to X3 are —N(H)—'s, and, as needed, the synthesis of a nitrogen fixation complex represented by formula (3) in which three of X1 to X3 are —N(H)—'s occur in stages, there may be stepwise increase in the number of moles of nitrogen molecules (or the pressure of nitrogen molecules) that are used at each stage.

In the process (A), hydrogen molecules may be brought into contact with the nitrogen fixation complex represented by formula (3) under any conditions. For example, hydrogen molecules may be brought into contact with the nitrogen fixation complex represented by formula (3) in the temperature range of −30° C. to 200° C. and at a pressure (partial pressure in the case of a mixture gas) of hydrogen molecules (hydrogen gas) in the range of 1 atm to 100 atm. The duration of contact (reaction) is not limited to a particular length of time. For example, the duration falls within the range of 1 hour to 24 hours. Hydrogen molecules need only be brought into contact with the nitrogen fixation complex represented by formula (3) as simple hydrogen molecules or as a component of a mixture gas. The mixture gas may be one that contains hydrogen molecules and nitrogen molecules, but is preferably one that contains more hydrogen molecules in number of moles.

Alternatively, in the process (B), hydrogen molecules and nitrogen molecules may be brought into contact with the complex represented by formula (1A) in a simultaneous parallel manner under any conditions. For example, hydrogen molecules and nitrogen molecules may be brought into contact with the complex represented by formula (1A) in the temperature range of 25° C. to 200° C. and at a pressure (partial pressure) of hydrogen molecules (hydrogen gas) in the range of 1 atm to 100 atm and a pressure (partial pressure) of nitrogen molecules (nitrogen gas) in the range of 1 atm to 100 atm. The duration of contact (reaction) is not limited to a particular length of time. For example, the duration falls within the range of 1 hour to 24 hours. It should be noted that a mixture gas containing other molecules in addition to the hydrogen molecules and the nitrogen molecules may be brought into contact with the complex represented by formula (3).

In the synthesis of ammonia by the process (B), too, ammonia is presumably synthesized from the complex represented by formula (1A) through the complex represented by formula (3). This makes it possible to continuously synthesize ammonia by continuously bringing hydrogen molecules and nitrogen molecules into contact with the complex represented by formula (1A) through continuous application of the process (B) to the complex.

Alternatively, ammonia may be synthesized by bringing a Lewis acid represented by formula $M5X_n$ into reaction with the nitrogen fixation complex represented by formula (3), which was obtained from the process (A) or (B), to form a Lewis acid complex represented by formula (3') to which a Lewis acid group has bonded and further applying the process (B) to the Lewis acid complex (3'). It should be noted here that M5 and X in the Lewis acid are identical to M5 and X in the complex (3'), respectively. Further, n is the number of X's binding to M5).

It should be noted that M5 in the Lewis acid is a polyvalent element, preferably a metal atom, e.g. an atom selected from among Cu (copper), Zn (zinc), Sc (scandium), and Y (yttrium), particularly from among Cu, Zn, and Sc. Further, an example of X is an atom selected from among F, Cl, Br, I, and $OSO_2CF_3$.

It is preferable that the Lewis acid be a metallic halide, more preferably one selected for example from among $CuCl$, $ZnCl_2$, $ScCl_3$ and $YCl_3$, particularly preferably $CuCl$, $ZnCl_2$, or $ScCl_3$.

Further, other examples of the Lewis acid include $Ag(OSO_2CF_3)$, a Lewis acid represented by formula $EX_3$ (which here is B, Al, Ga, or In and where X is F, Cl, Br, I, Ph (phenyl group), or $C_6F_5$), a Lewis acid represented by formula $EX_2$ (which here is Ge or Sn and where X is F, Cl, Br, I, Ph, or $C_6F_5$), and a Lewis acid containing a transition metal atom, such as $FeCl_2$, $RuCl_3$, $RhCl_3$, $IrCl_3$, $PdCl_2$, or $PtCl_2$.

The Lewis acid may be brought into contact with the complex represented by formula (3) under any conditions. For example, stirring at a temperature in the range of 20° C. to 80° C. for a period of time in the range of 1 hour to 12 hours may be followed by still standing at a temperature in the range of −35° C. to 20° C. for a period of time in the range of 1 hour to 24 hours.

The complex represented by formula (1A) or the nitrogen fixation complex represented by formula (3) may be used while being dissolved in a solvent or while being in the form a solid. Examples of the solvent include hexane, pentane, heptane, a mixed solvent obtained by mixing two or more of these solvents, and the like. The complex may be used while being fixed to a carrier Examples of the carrier include silica gel, alumina (aluminum oxide), active carbon, titania (titanium dioxide), and the like. The carrier may alternatively be an electride obtained by incorporating electrons into a $12CaO\cdot7Al_2O_3$ structure.

The synthesis of ammonia with use or a cationic or anionic complex from the complex represented by formula (1A) can be performed under substantially the same conditions as the synthesis of ammonia with use of the complex represented by formula (1A). Further, the synthesis of ammonia with use of the complex represented by formula (1B) or a cationic or anionic complex from the complex, too, can be performed according to the method for synthesizing ammonia with use of the complex represented by formula (1A).

[4. Other Applications]

The present invention provides a fixed bed for use in ammonia synthesis. This fixed bed is obtained by fixing a complex represented by formula (1A), a complex represented by formula (1B), a cationic or anionic complex from any of these complexes, or a nitrogen fixation complex represented by formula (3). The fixed bed may be configured such that any of these complexes or the nitrogen fixation complex is fixed as a solid to a column, the carrier, or the like or bonded to the carrier while being dissolved in the solvent (see FIG. 1).

Further, the present invention provides an ammonia synthesis apparatus including the fixed bed described above (see FIG. 1). It is preferable that the ammonia synthesis apparatus further include hydrogen supply equipment and nitrogen supply equipment.

EXAMPLES

1. Materials and Methods

All reactions were carried out under a dry and oxygen-free argon atmosphere by using Schlenk techniques or a nitrogen or argon atmosphere in an Mbraun glovebox. The argon was purified by being passed through a Dryclean column (4 Å molecular sieves, Nikka Seiko Co.) and a Gasclean GC-XR column (Nikka Seiko Co.). The nitrogen and the argon in the glovebox were constantly circulated through a copper/molecular sieve catalyst unit. The oxygen and moisture concentrations were monitored by an $O_2/H_2O$ Combi-Analyzer (Mbraun) to ensure both were always below 1 ppm. Samples for NMR spectroscopic measurements were prepared by using Schlenk techniques or in the glovebox by use of J. Young valve NMR tubes. $^1H$, $^{13}C$, and $^{15}N$ NMR spectra were recorded on a JEOL-AL400, a JNM-AL300, or JNM-ECA600 spectrometer. IR spectra were recorded on a Shimazu IRPrestige-21 spectrometer using nujol mulls between KBr disks. Elemental analyses were performed by a MICRO CORDER JM10. Anhydrous THF, hexane, benzene, $Et_2O$, and toluene were purified by use of a SPS-800 solvent purification system (Mbraun), and dried over fresh new Na chips in the glovebox. $C_5Me_4H(SiMe_3)$ was purchased from Aldrich, and used as received. Other reagents ($TiCl_4$ and $LiCH_2SiMe_3$) were used as received.

2. Reference Example

For abbreviated designations of the following compounds, see chemical formulas in section [3. Example] below.

(($C_5Me_4SiMe_3$)Ti($CH_2SiMe_3$)$_3$: Complex 1-Ti)

$LiCH_2SiMe_3$ (812 mg, 8.63 mmol) was slowly added to a stirred suspension of [($C_5Me_4SiMe_3$)$TiCl_3$](1.0 g, 2.88 mmol) in toluene at −40° C. The mixture was then warmed to room temperature and stirred for 3 minutes. After removal of the solvent under vacuum, the residual solid was extracted with hexane and filtrated. After reduction of the solution volume under reduced pressure, the orange-colored solution was cooled at −33° C. overnight to give a complex 1-Ti (908 mg, 1.81 mmol, 63%) as pale yellow crystals.

Complex 1-Ti: $^1H$ NMR ($C_6D_6$, rt): 2.05 (s, 6H, $C_5Me_4SiMe_3$), 1.83 (s, 6H, $C_5Me_4SiMe_3$), 1.45 (s, 6H, $TiCH_2SiMe_3$), 0.27 (s, 36H, $C_5Me_4SiMe_3$, $TiCH_2SiMe_3$). $^{13}C$ NMR ($C_6D_6$, rt): 128.4 (s, $C_5Me_4SiMe_3$), 127.5 (s, $C_5Me_4SiMe_3$), 122.6 (s, ipso-$C_5Me_4SiMe_3$), 85.8 (s, $TiCH_2SiMe_3$), 16.0 (s, $C_5Me_4SiMe_3$), 13.07 (s, $C_5Me_4SiMe_3$), 3.0 (s, $TiCH_2SiMe_3$), 1.9 (s, $C_5Me_4SiMe_3$). Anal. Calcd for $C_{24}H_{54}Si_4Ti$: C, 57.32; H, 10.82. Found: C, 57.32; H, 10.50.

(($C_5Me_4SiMe_3$)$_4Ti_4(\mu_3$-NH)$_2(\mu$-H)$_4$: Complex 3)

A hexane solution (2.0 mL) of the complex 1-Ti (100 mg, 0.199 mmol) in 10 mL Hiper Glass Cylinder (TAIATSU TECHNO (registered trademark)) was filled with 1 atm of $N_2$ and 4 atm of $H_2$. The solution was stirred at 60° C. for 1 day. The color of the solution changed from pale yellow to dark purple. After the reaction, the solution was evaporated and the residue was washed with cold hexane to give a complex 3 (45 mg, 0.045 mmol, 90%) as a dark purple solid. Single crystals of the complex 3 suitable for X-ray diffraction study were obtained from the concentrated $C_6H_6$ solution of the complex 3 at room temperature. The preparation of the $^{15}N$-enriched compound [($C_5Me_4SiMe_3$)$_4Ti_4(\mu_3$-$^{15}NH$)$_2(\mu$-H)$_4$]: complex 3-$^{15}N$ was carried out in exactly the same manner as for the parent complex 3.

Complex 3: $^1H$ NMR ($C_6D_6$, rt): 11.01 (s, 2H, $\mu_3$-NH), 2.27 (s, 12H, $C_5Me_4SiMe_3$), 2.03 (s, 12H, $C_5Me_4SiMe_3$), 1.91 (s, 12H, $C_5Me_4SiMe_3$), 1.88 (s, 12H, $C_5Me_4SiMe_3$), 1.82 (s, 4H, $\mu$-H), 0.49 (s, 18H, $C_5Me_4SiMe_3$), 0.34 (s, 18H, $C_5Me_4SiMe_3$). $^{13}C$ NMR ($C_6D_6$, rt): 126.4 (s, $C_5Me_4SiMe_3$), 125.6 (s, $C_5Me_4SiMe_3$), 123.2 (s, $C_5Me_4SiMe_3$), 122.2 (s, $C_5Me_4SiMe_3$), 115.4 (s, ipso-$C_5Me_4SiMe_3$), 114.7 (s, ipso-$C_5Me_4SiMe_3$), 16.9 (s, $C_5Me_4SiMe_3$), 13.9 (s, $C_5Me_4SiMe_3$), 13.3 (s, $C_5Me_4SiMe_3$), 3.2 (s, $C_5Me_4SiMe_3$), 3.0 (s, $C_5Me_4SiMe_3$). Calcd for $C_{48}H_{90}N_2Si_4Ti_4$: C, 57.71; H, 9.08; N, 2.80. Found: C, 58.11; H, 8.78; N, 2.75.

Complex 3-$^{15}N$: $^1H$ NMR ($C_6D_6$, rt): 11.04 (d, $J_{NH}$=66.5 Hz, $^{15}NH$), 2.28 (s, 12H, $C_5Me_4SiMe_3$), 2.04 (s, 12H, $C_5Me_4SiMe_3$), 1.92 (s, 12H, $C_5Me_4SiMe_3$), 1.89 (s, 12H, $C_5Me_4SiMe_3$), 1.76 (s, 4H, $\mu$-H), 0.50 (s, 18H, $C_5Me_4SiMe_3$), 0.35 (s, 18H, $C_5Me_4SiMe_3$). $^{13}C$ NMR ($C_6D_6$, rt): 126.4 (s, $C_5Me_4SiMe_3$), 125.6 (s, $C_5Me_4SiMe_3$), 123.2 (s, $C_5Me_4SiMe_3$), 122.2 (s, $C_5Me_4SiMe_3$), 115.4 (s, ipso-$C_5Me_4SiMe_3$), 114.7 (s, ipso-$C_5Me_4SiMe_3$), 16.9 (s, $C_5Me_4SiMe_3$), 13.9 (s, $C_5Me_4SiMe_3$), 13.4 (s, $C_5Me_4SiMe_3$), 3.2 (s, $C_5Me_4SiMe_3$), 3.0 (s, $C_5Me_4SiMe_3$). $^{15}N$ NMR (60.81 MHz, $C_6D_6$, $MeNO_2$, rt): σ 52.7 (s, $J_{NH}$=66.8 Hz, $\mu_3$-NH).

(($C_5Me_4SiMe_3$)$_4Ti_4(\mu$-H)$_8$: Complex 2-Ti)

A hexane solution (2.0 mL) of the complex 1-Ti (252 mg, 0.501 mmol) in 10 mL Hiper Glass Cylinder (TAIATSU TECHNO (registered trademark)) was filled with $H_2$ (4 atm). The pale yellow solution was stirred at 60° C. for 17 hours. After the reaction, the solution changed to dark red, which was evaporated and crystallized in THF at −33° C. to give a complex 2-Ti (12 mg, 0.012 mmol, 10%) as a dark brown solid. Single crystal of the complex 2-Ti suitable for X-ray diffraction study were obtained from the concentrated $C_6H_6$ solution at room temperature.

Complex 2-Ti: $^1H$ NMR ($C_6D_6$, rt): 2.41 (s, 24H, $C_5Me_4SiMe_3$), 2.28 (s, 24H, $C_5Me_4SiMe_3$), 0.52 (s, 36H, $C_5Me_4SiMe_3$), −1.21 (s, 8H, $\mu$-H). $^{13}C$ NMR ($C_6D_6$, rt): 127.1 (s, $C_5Me_4SiMe_3$), 122.4 (s, $C_5Me_4SiMe_3$), 114.2 (s, ipso-$C_5Me_4SiMe_3$), 18.3 (s, $C_5Me_4SiMe_3$), 14.1 (s, $C_5Me_4SiMe_3$), 3.7 (s, $C_5Me_4SiMe_3$). Calcd for $C_{48}H_{92}Si_4Ti_4$: C, 59.25; H, 9.53. Found: C, 59.07; H, 8.69.

(X-Ray Crystallographic Studies of the Complex 3 and the Complex 2-Ti)

Crystals for X-ray analysis were obtained in the manner described above. The crystals were manipulated in the glovebox under a microscope in the glovebox, and were sealed in thin-walled glass capillaries. Data collection was performed at −100° C. on Bruker SMART APEX diffractometer with CCD area detector, using graphite monochromated Mo—Kα radiation (λ=0.71073 Å). The determination of crystal class and unit cell parameters was carried out by the SMART program package. Raw frame data were processed using SAINT and SADABS to yield a data file. The structure was solved by using SHELXTL program. Refinement for the complexes 2-Ti and 3 was performed on $F^2$ anisotropically for non-hydrogen atoms by the full-matrix least-squares methods. The analytical scattering factors for neutral atoms were used throughout the analysis. Disorder at the H5 and H6 atoms in the complex 2-Ti was refined at 50% occupancy. Disorder at the N1, N2, H2, H3, H4, and H5 atoms in the complex 3 was refined at 50% occupancy. The residual electron densities were of no chemical significance.

Figure 2:
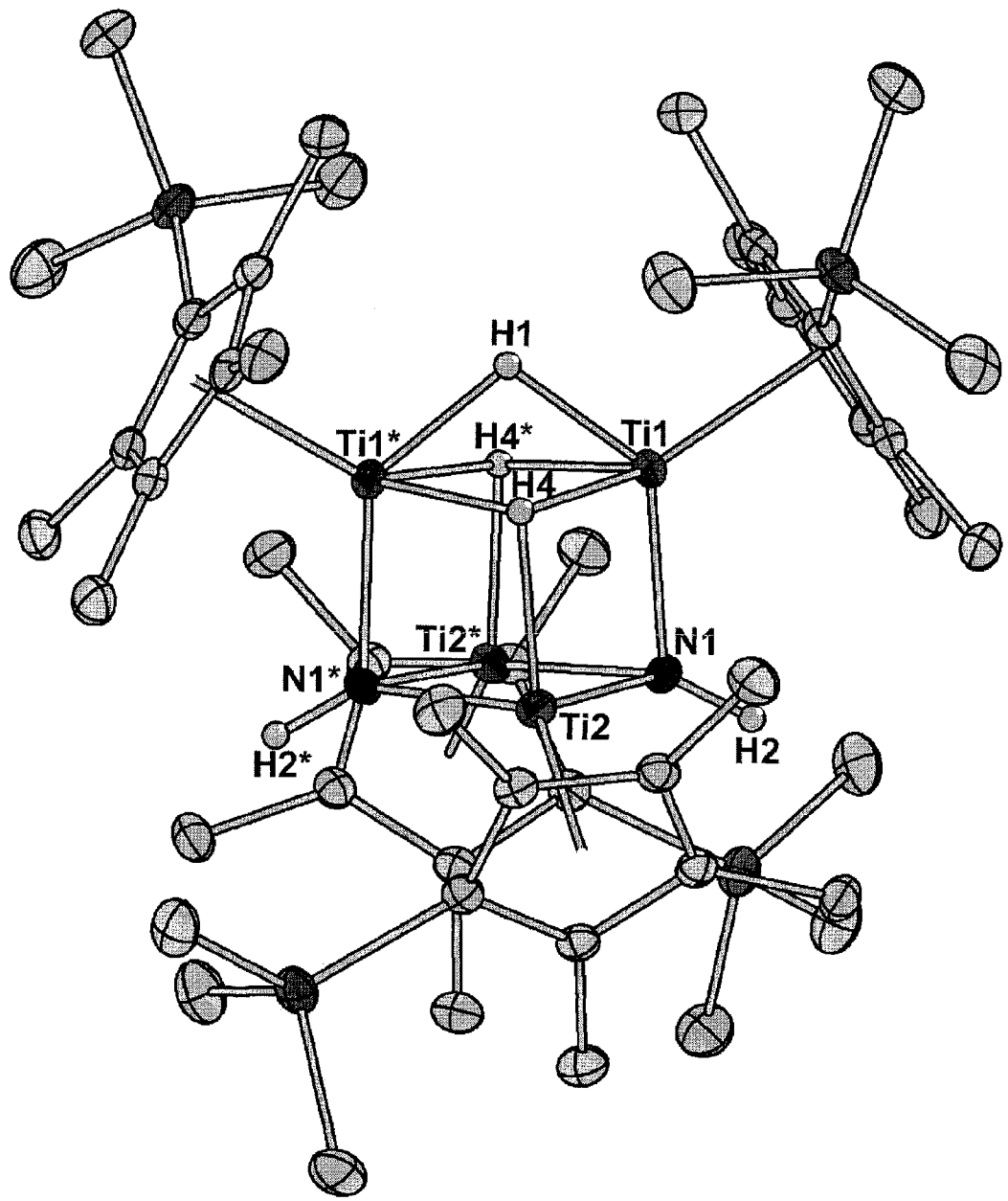
FIG. 2 shows a crystal structure of a complex molecule according to a reference example.
Figure 3:
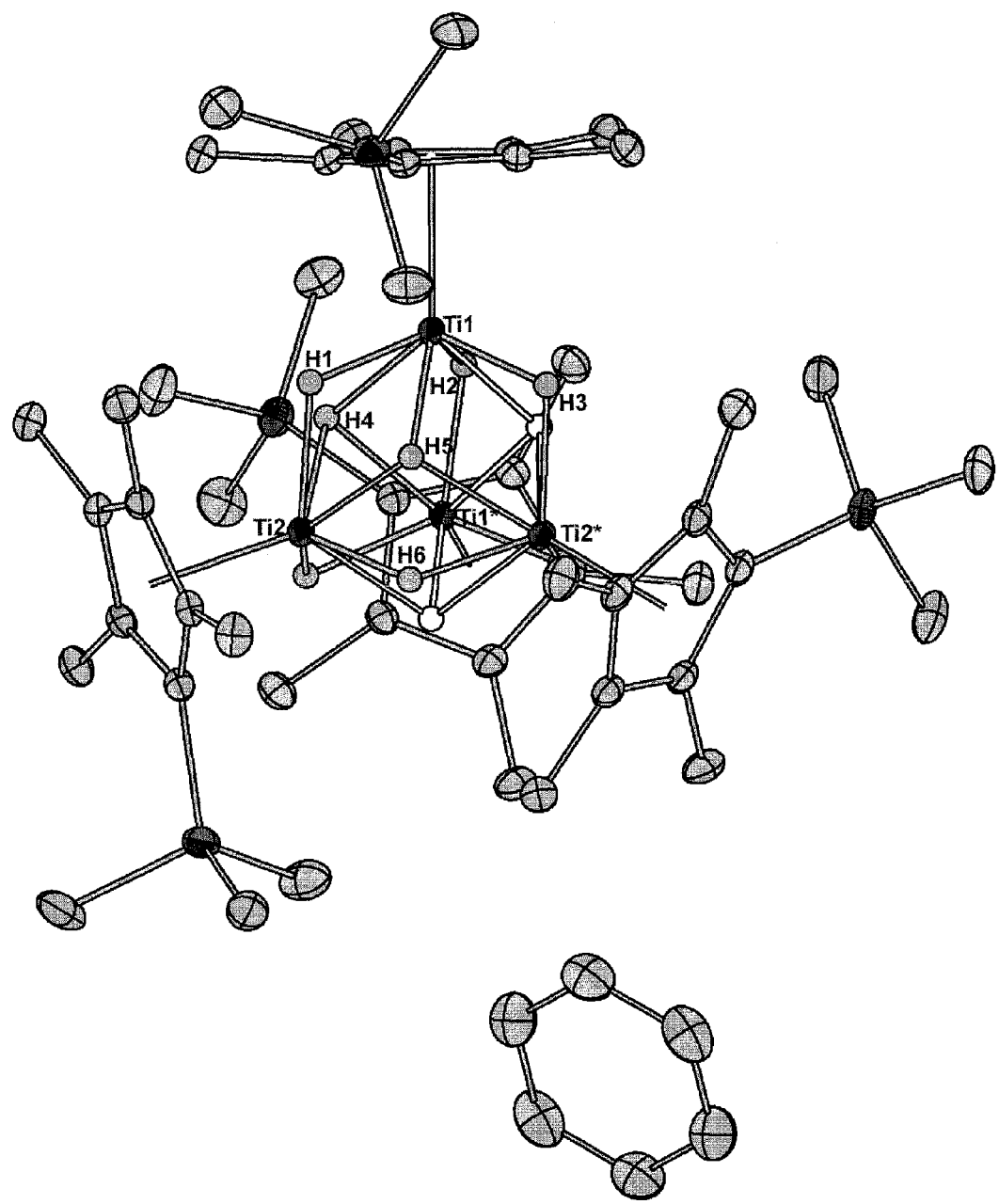
FIG. 3 shows a crystal structure of a complex molecule according to the reference example.

FIGS. 2 and 3 show models of crystal structures obtained as a result of the foregoing analysis, respectively. FIG. 2 shows a result of the X-ray crystallographic study of the complex 3. For the purpose of clarification, FIG. 2 omits to show two μ₃-imino ligands having disorders in position. FIG. 3 shows a result of the X-ray crystallographic study of the complex 2-Ti.

3. Example 1

[Chem. 17]

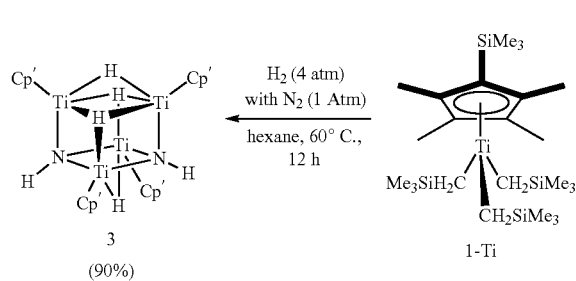
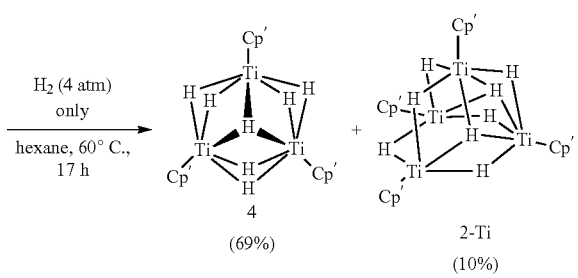

((C₅Me₄SiMe₃)₃Ti₃(μ-H)₇: Complex 4)

Figure 4:
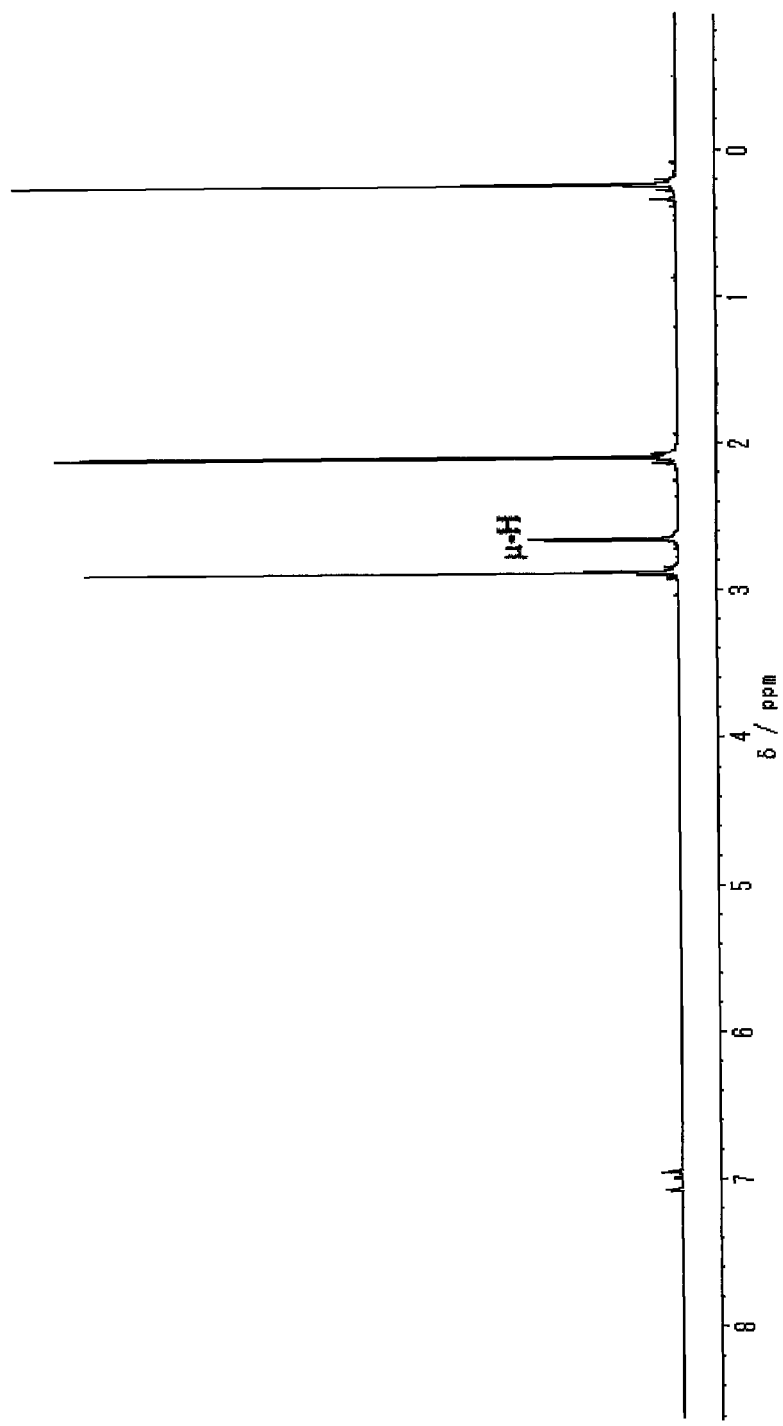
FIG. 4 shows the NMR spectrum of a complex molecule according to an example.

After the complex 2-Ti had been crystallized from a product obtained according to the same procedure as the synthesis of the complex 2-Ti, the residual solution portion was evaporated under reduced pressure and crystallized in hexane at −33° C. to give a complex 4 (84 mg, 0.115 mmol, 69%) as a dark purple solid. Single crystals of the complex 4 suitable for X-ray diffraction study were obtained from the concentrated THF solution of the complex 4 at −33° C. FIG. 4 shows a ¹H NMR spectrum (400 MHz, Toluene-d₈, room temperature) of the complex 4.

Complex 4: $^1$H NMR (Toluene-d$_8$, rt): 2.88 (s, 18H, C$_5$Me$_4$SiMe$_3$), 2.66 (s, 7H, μ-H), 2.10 (s, 18H, C$_5$Me$_4$SiMe$_3$), 0.25 (s, 27H, C$_5$Me$_4$SiMe$_3$). $^{13}$C NMR (Toluene-d$_8$, rt): 129.1 (obscured by Toluene-d$_8$, C$_5$Me$_4$SiMe$_3$), 123.3 (s, C$_5$Me$_4$SiMe$_3$), 113.0 (s, ipso-C$_5$Me$_4$SiMe$_3$), 17.2 (s, C$_5$Me$_4$SiMe$_3$), 12.9 (s, C$_5$Me$_4$SiMe$_3$), 2.5 (s, C$_5$Me$_4$SiMe$_3$). $^1$H NMR (THF-d$_8$, rt): 2.85 (s, 18H, C$_5$Me$_4$SiMe$_3$), 2.53 (s, 7H, μ-H), 2.12 (s, 18H, C$_5$Me$_4$SiMe$_3$), 0.12 (s, 27H, C$_5$Me$_4$SiMe$_3$). $^{13}$C NMR (THF-d$_8$, rt): 129.6 (s, C$_5$Me$_4$SiMe$_3$), 123.8 (s, C$_5$Me$_4$SiMe$_3$), 113.4 (s, ipso-C$_5$Me$_4$SiMe$_3$), 17.5 (s, C$_5$Me$_4$SiMe$_3$), 13.0 (s, C$_5$Me$_4$SiMe$_3$), 2.6 (s, C$_5$Me$_4$SiMe$_3$). Calcd for C$_{36}$H$_{70}$Si$_3$Ti$_3$: C, 59.17; H, 9.65. Found: C, 58.93; H, 8.79.

((C₅Me₄SiMe₃)₃Ti₃(μ₃-N)(μ-NH)(μ-H)₂: Complex 7)

In the N₂ glovebox, the complex 4 (101 mg, 0.138 mmol) was dissolved in hexane (1.5 mL) at room temperature for 12 hours. The solution turned from brown to dark purple. After the reaction, the solution was concentrated and crystallized at −33° C. to precipitate a complex 7 (94 mg, 0.125 mg, 91%) as a dark purple solid. Single crystals of a THF-coordinated complex 7-THF suitable for X-ray diffraction study were obtained from THF solution at −33° C.

Complex 7: $^1$H NMR (Toluene-d$_8$, rt): 37.65 (brs, 1H, NH), 11.69 (s, 6H, C$_5$Me$_4$SiMe$_3$), 6.93 (s, 6H, C$_5$Me$_4$SiMe$_3$), 4.21 (s, 6H, C$_5$Me$_4$SiMe$_3$), 3.99 (s, 6H, C$_5$Me$_4$SiMe$_3$), 3.92 (s, 6H, C$_5$Me$_4$SiMe$_3$), 3.89 (s, 6H, C$_5$Me$_4$SiMe$_3$), 0.58 (s, 18H, C$_5$Me$_4$SiMe$_3$), 0.42 (s, 9H, C$_5$Me$_4$SiMe$_3$). $^1$H NMR (THF-d$_8$, −70° C.): 17.23 (brs, 1H, NH), 2.48 (s, 6H, C$_5$Me$_4$SiMe$_3$), 2.13 (s, 12H, C$_5$Me$_4$SiMe$_3$), 2.08 (s, 6H, C$_5$Me$_4$SiMe$_3$), 1.95 (s, 6H, C$_5$Me$_4$SiMe$_3$), 1.89 (s, 6H, C$_5$Me$_4$SiMe$_3$), 0.19 (s, 18H, C$_5$Me$_4$SiMe$_3$), 0.01 (s, 9H, C$_5$Me$_4$SiMe$_3$).

7-$^{15}$N: $^1$H NMR (Toluene-d$_8$, rt): 37.46 (d, J$_{HN}$=65.2 Hz, 1H, $^{15}$N—H), 11.62 (s, 6H, C$_5$Me$_4$SiMe$_3$), 6.91 (s, 6H, C$_5$Me$_4$SiMe$_3$), 4.20 (s, 6H, C$_5$Me$_4$SiMe$_3$), 3.98 (s, 6H, C$_5$Me$_4$SiMe$_3$), 3.92 (s, 6H, C$_5$Me$_4$SiMe$_3$), 3.88 (s, 6H, C$_5$Me$_4$SiMe$_3$), 0.59 (s, 18H, C$_5$Me$_4$SiMe$_3$), 0.43 (s, 9H, C$_5$Me$_4$SiMe$_3$). $^1$H NMR (THF-d$_8$, −50° C.): 17.62 (d, J$_{HN}$=63.6 Hz, 1H, $^{15}$N—H), 2.59 (s, 6H, C$_5$Me$_4$SiMe$_3$), 2.32 (s, 6H, C$_5$Me$_4$SiMe$_3$), 2.19 (s, 6H, C$_5$Me$_4$SiMe$_3$), 2.15 (s, 6H, C$_5$Me$_4$SiMe$_3$), 2.07 (s, 6H, C$_5$Me$_4$SiMe$_3$), 2.01 (s, 6H, C$_5$Me$_4$SiMe$_3$), 0.17 (s, 18H, C$_5$Me$_4$SiMe$_3$), −0.01 (s, 9H, C$_5$Me$_4$SiMe$_3$). $^{15}$H NMR (40.5 MHz, THF-d$_8$, MeNO$_2$, −50° C.): σ 402.9 (s, μ-N), 46.9 (s, μ-NH). Calcd for C$_{36}$H$_{66}$N$_2$Si$_3$Ti$_3$: C, 57.29; H, 8.81; N, 3.71. Found: C, 57.77; H, 8.73; N, 3.30.

[Chem. 18]

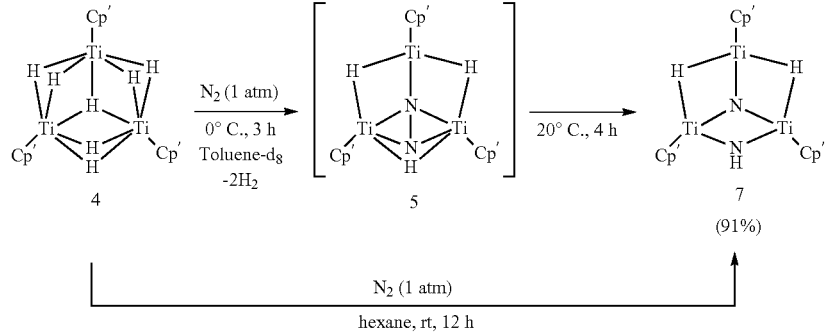

(X-Ray Crystallographic Study of the Complex 4 and the Complex 7)

As with the complex 3 and the complex 2-Ti, the complex 4 and the complex 7 were subjected to X-ray crystallographic study. Disorder at the H7 atom in the complex 4 among the analysis results was refined at 61% occupancy. The residual electron densities were of no chemical significance. Crystal data and analysis results including the complex 3 and the complex 2-Ti are listed in Table 1.

$C_5Me_4SiMe_3$), 1.81 (s, 6H, $C_5Me_4SiMe_3$), 1.66 (s, 6H, $C_5Me_4SiMe_3$), 0.27 (s, 18H, $C_5Me_4SiMe_3$), 0.01 (s, 9H, $C_5Me_4SiMe_3$), −13.69 (s, 2H, Ti—H—Ti).

5-$^{15}$N: $^{15}$N NMR (60.81 MHz, Toluene-$d_8$, MeNO$_2$, −30° C.): 262.8 (d, $J_{NN}$=21.0 Hz, N—N), 73.0 (d, $J_{NN}$=21.0 Hz, N—N).

5-$d_3$: $^2$H NMR (62 MHz, Toluene-$d_8$, −30° C.): 10.3 (s, 1D, μ-D), −13.9 (s, 2D, μ-D).

TABLE 1

|  | 2-Ti | 3 | 4 | 7-THF |
|---|---|---|---|---|
| formula | $C_{48}H_{92}Si_4Ti_4 \cdot C_6H_6$ | $C_{48}H_{89}N_2Si_4Ti_4 \cdot C_6H_6$ | $C_{36}H_{70}Si_3Ti_3$ | $C_{40}H_{74}N_2OSi_3Ti_3$ |
| formula weight | 1051.28 | 1075.27 | 730.89 | 826.98 |
| crystal system | Monoclinic | Monoclinic | Monoclinic | Triclinic |
| space group | C2/c | C2/c | P2$_1$/n | P-1 |
| a, Å | 24.170(4) | 24.230(2) | 11.130(2) | 10.001(4) |
| b, Å | 12.0995(17) | 12.1088(10) | 18.990(3) | 12.717(5) |
| c, Å | 21.178(3) | 21.3889(18) | 19.587(4) | 18.445(8) |
| α, deg |  |  |  | 95.274(8) |
| β, deg | 109.124(4) | 108.5300(10) | 90.426(2) | 90.099(7) |
| γ, deg |  |  |  | 90.002(7) |
| V, Å$^3$ | 5851.4(15) | 5950.2(9) | 4139.6(13) | 2335.8(17) |
| Z | 4 | 4 | 4 | 2 |
| D$_{calcd}$, g/cm$^3$ | 1.193 | 1.200 | 1.173 | 1.176 |
| temp, K | 173(2) | 173(2) | 173(2) | 173(2) |
| μ, mm$^{-1}$ (MoKα) | 0.640 | 0.632 | 0.673 | 0.607 |
| 2θ$_{max}$ | 54.0 | 55.0 | 54.0 | 54.0 |
| reflections collected | 17739 | 18144 | 24221 | 14103 |
| independent reflections (R$_{int}$) | 6309 (0.1111) | 6740 (0.0204) | 8898 (0.0283) | 9791 (0.1014) |
| R1 (I > 2σ(I)) | 0.0589 | 0.0309 | 0.0334 | 0.1044 |
| wR2 (I > 2σ(I)) | 0.1637 | 0.0887 | 0.0907 | 0.2618 |
| wR2 (all data) | 0.1679 | 0.0924 | 0.0955 | 0.2811 |
| parameters | 308 | 314 | 433 | 445 |
| GOF | 1.029 | 1.017 | 1.017 | 0.943 |

Figure 5:
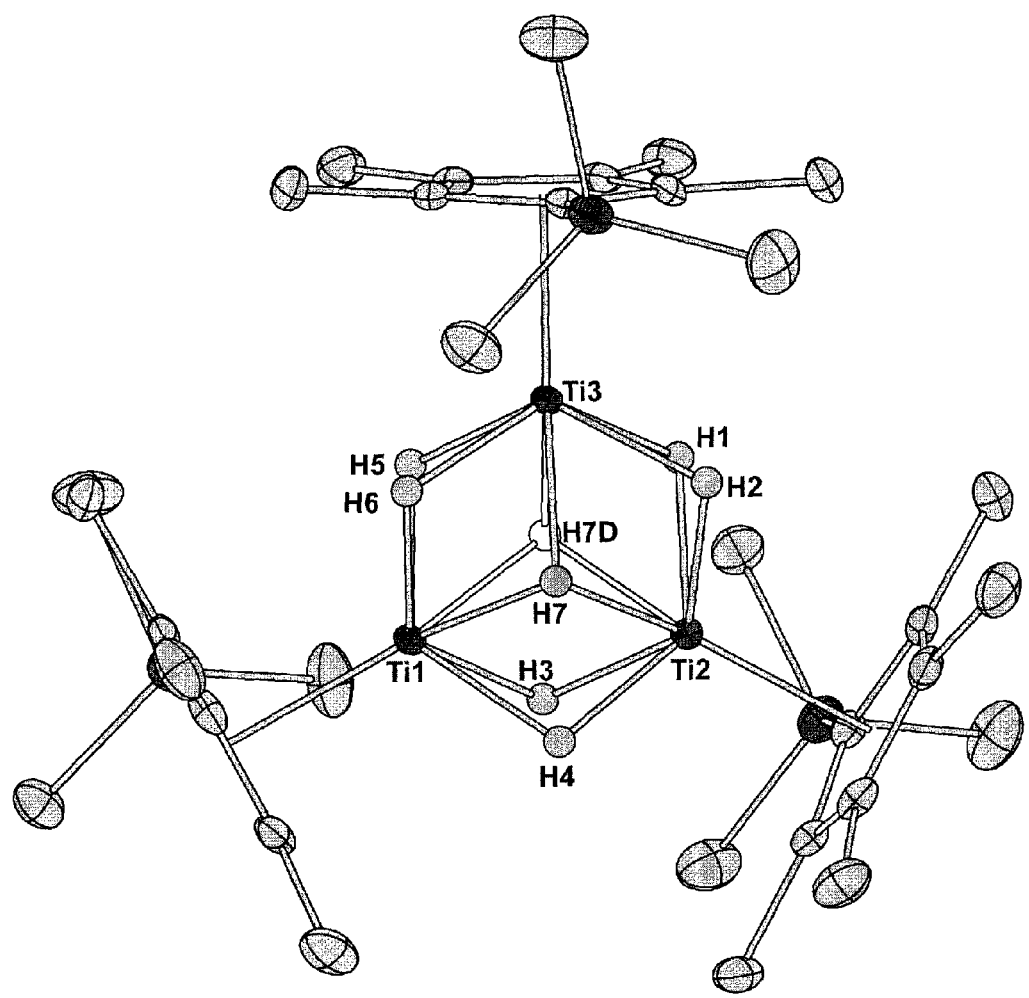
FIG. 5 shows a crystal structure of a complex molecule according to the example.
Figure 6:
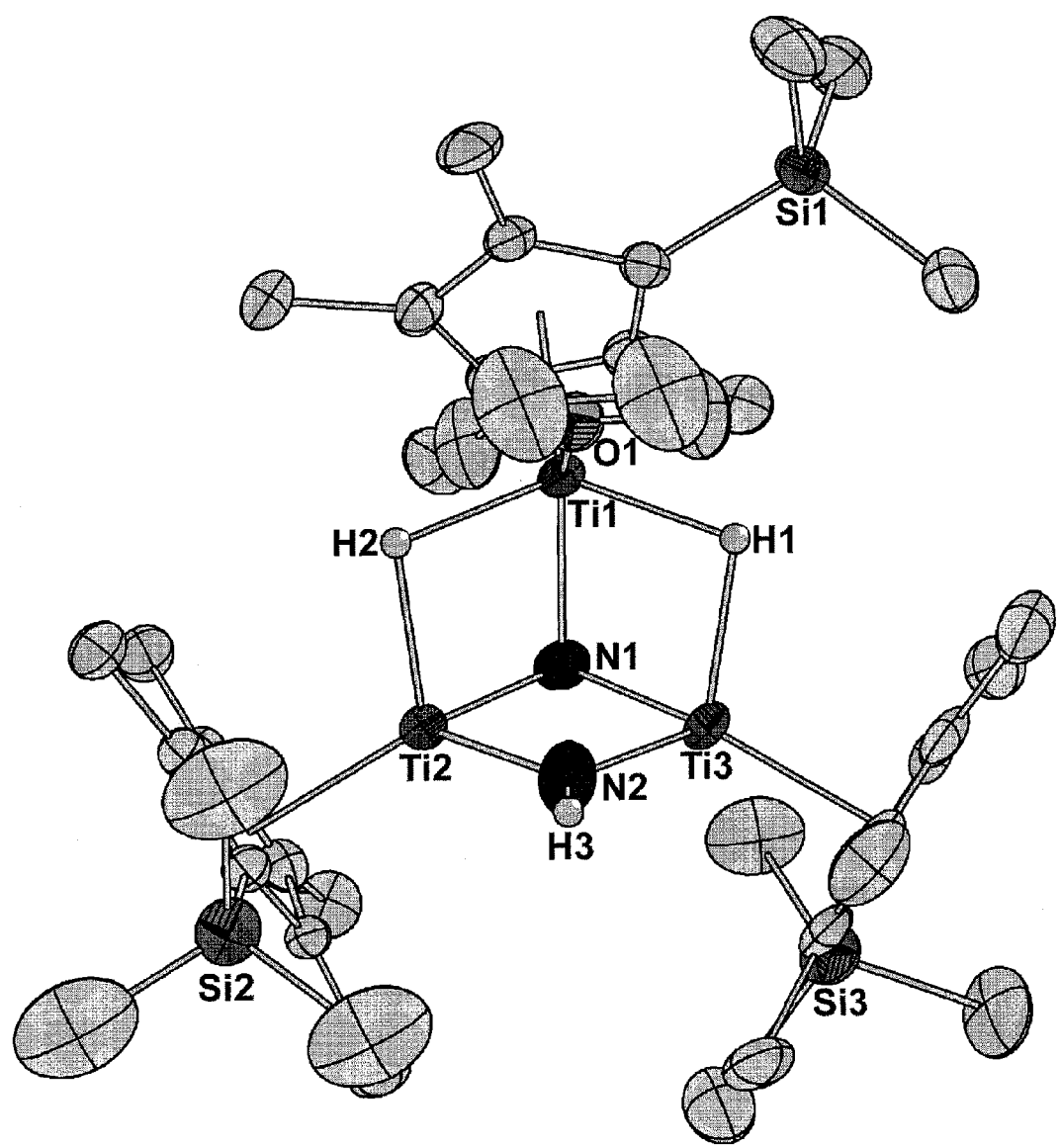
FIG. 6 shows a crystal structure of a complex molecule according to the example.

FIGS. 5 and 6 show models of crystal structures 4 and 7 obtained as a result of the foregoing analysis, respectively. FIG. 5 shows a result of the X-ray structural analysis (H7:H7D=61:39) of the complex 4. FIG. 6 shows a result of the X-ray structural analysis of the complex 7 (complex 7-THF).

(Reaction of the Complex 4 with N$_2$ in Toluene-d$_8$)

Figure 7:
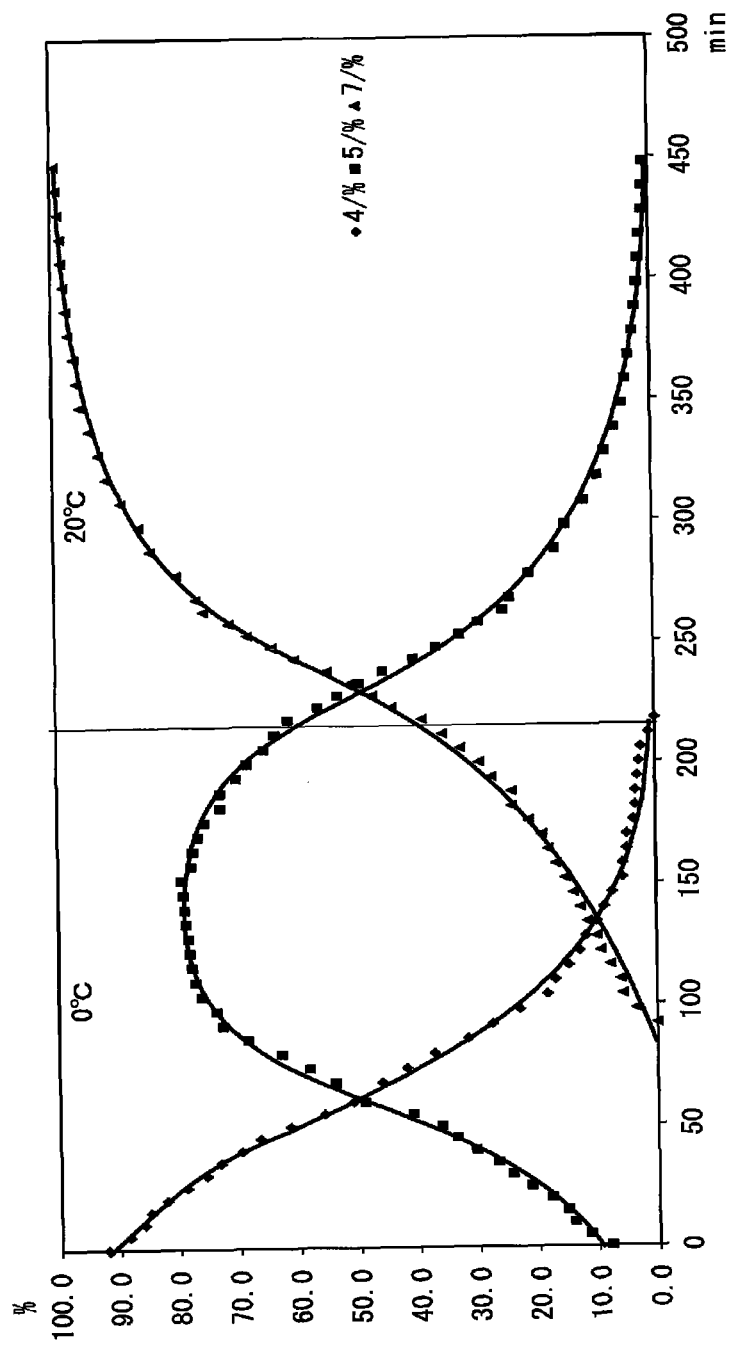
FIG. 7 shows a time-conversion curve of a complex molecule according to the example.

A J. Young valve NMR sample tube was charged with 0.5 mL of toluene-d$_8$ and the complex 4 (10 mg, 0.014 mmol). The solution was frozen in liquid nitrogen and degassed, and 1 atm of N$_2$ gas was added. The solution was kept at −0° C., and the reaction was monitored by $^1$H NMR. After 3 hours, the complex 4 was converted to an intermediate 5 (75% or lower) and an intermediate 7 (10% or lower) with the formation of H$_2$ (σH 4.5). Then, the temperature was increased from 0 to −20° C. After 4 hours, the intermediate 5 was converted to a complex 7 (95% or lower). FIG. 7 shows a time-conversion curve of the complex 4 with N$_2$. FIG. 7 is a time-conversion curve regarding the reaction between the complex 4 and N2 in THF-d$_8$ (0° C.: 0 to 212 min, 20° C.: 212 to 448 min).

NMR data for the reaction intermediate (C$_5$Me$_4$SiMe$_3$)$_3$Ti$_3$(μ-η$^1$:η$^2$:η$^2$-N$_2$)(μ-H)$_3$ (intermediate 5) is as indicated below.

Intermediate 5: $^1$H NMR (Toluene-d$_8$, 0° C.): 10.20 (s, 1H, Ti—H), 2.56 (s, 6H, C$_5$Me$_4$SiMe$_3$), 2.01 (s, 6H, C$_5$Me$_4$SiMe$_3$), 1.93 (s, 6H, C$_5$Me$_4$SiMe$_3$), 1.89 (s, 6H, (Reaction of the Complex 4 with N$_2$ in THF-d$_8$)

[Chem. 19]

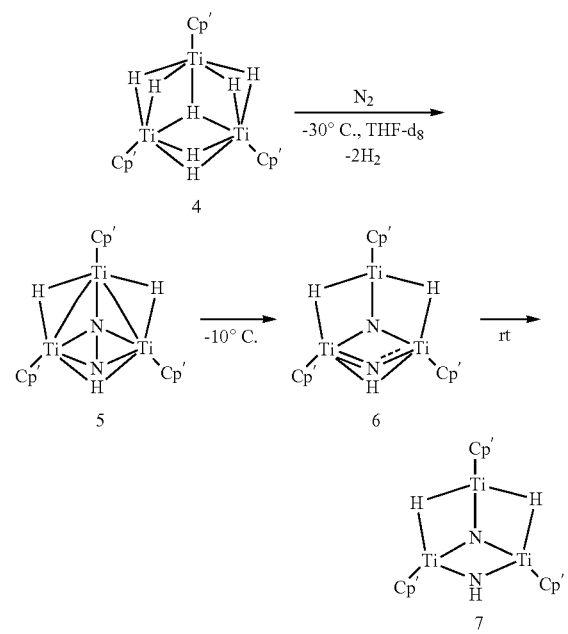

A J. Young valve NMR sample tube was charged with 0.5 mL of THF-$d_8$ and the complex 4 (15 mg, 0.019 mmol). The solution was frozen in liquid nitrogen and degassed, and 1 atm of $N_2$ gas was added. The solution was kept at $-30°$ C., and the reaction was monitored by $^1$H NMR. After 42 minutes, the complex 4 was converted to an intermediate 5 (80% or lower) and an intermediate 7 (10% or lower) with the formation of $H_2$ (σH 4.5). Then, the temperature was increased from $-30$ to $-10°$ C. After 3 hours, the interme-

[Chem. 20]

Figure 8:
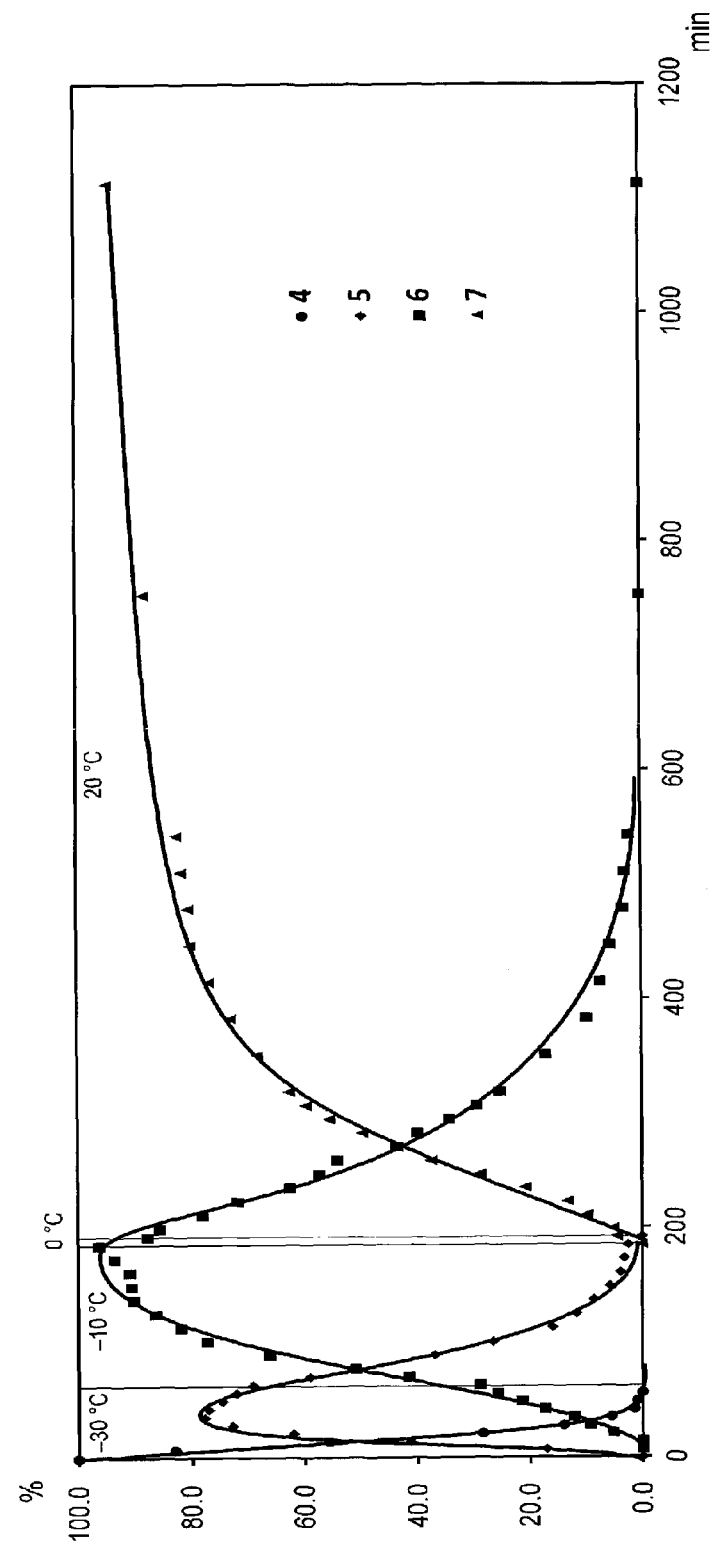
FIG. 8 shows a time-conversion curve of a complex molecule according to the example.

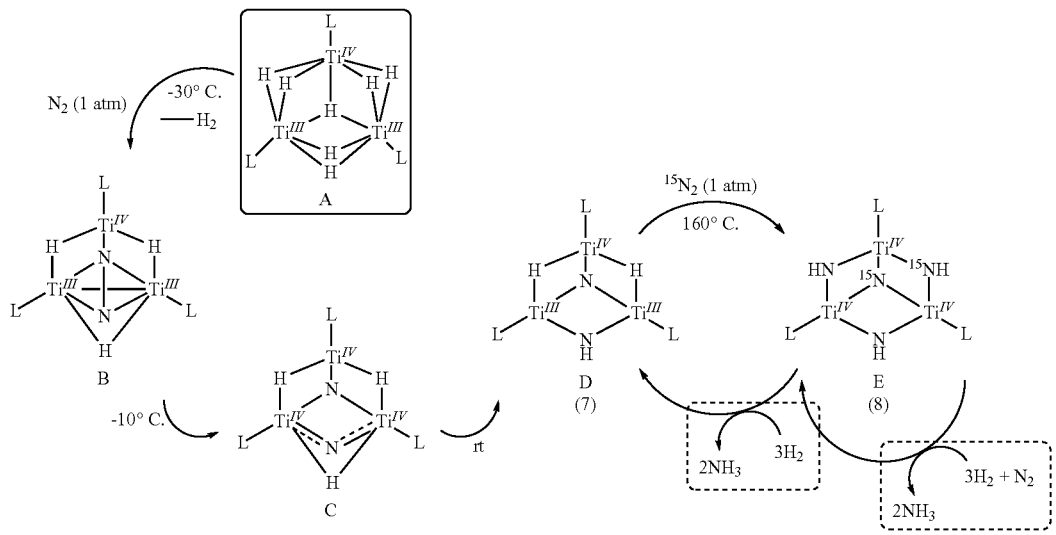

diate 5 was converted to a complex 6 (95% or lower). Finally, the temperature was raised to 20° C. After 19 hours, the complex 6 was completely converted to the intermediate 7 (94% or lower). FIG. 8 shows a time-conversion curve of the complex 4 with $N_2$. FIG. 8 is a time-conversion curve regarding the reaction between the complex 4 and N2 in THF-$d_8$ ($-30°$ C.: 0 to 63 min, $-10°$ C.: 63 to 185 min, 0° C.: 185 to 192 min, 20° C.: 192 to 1113 min).

Figure 9:
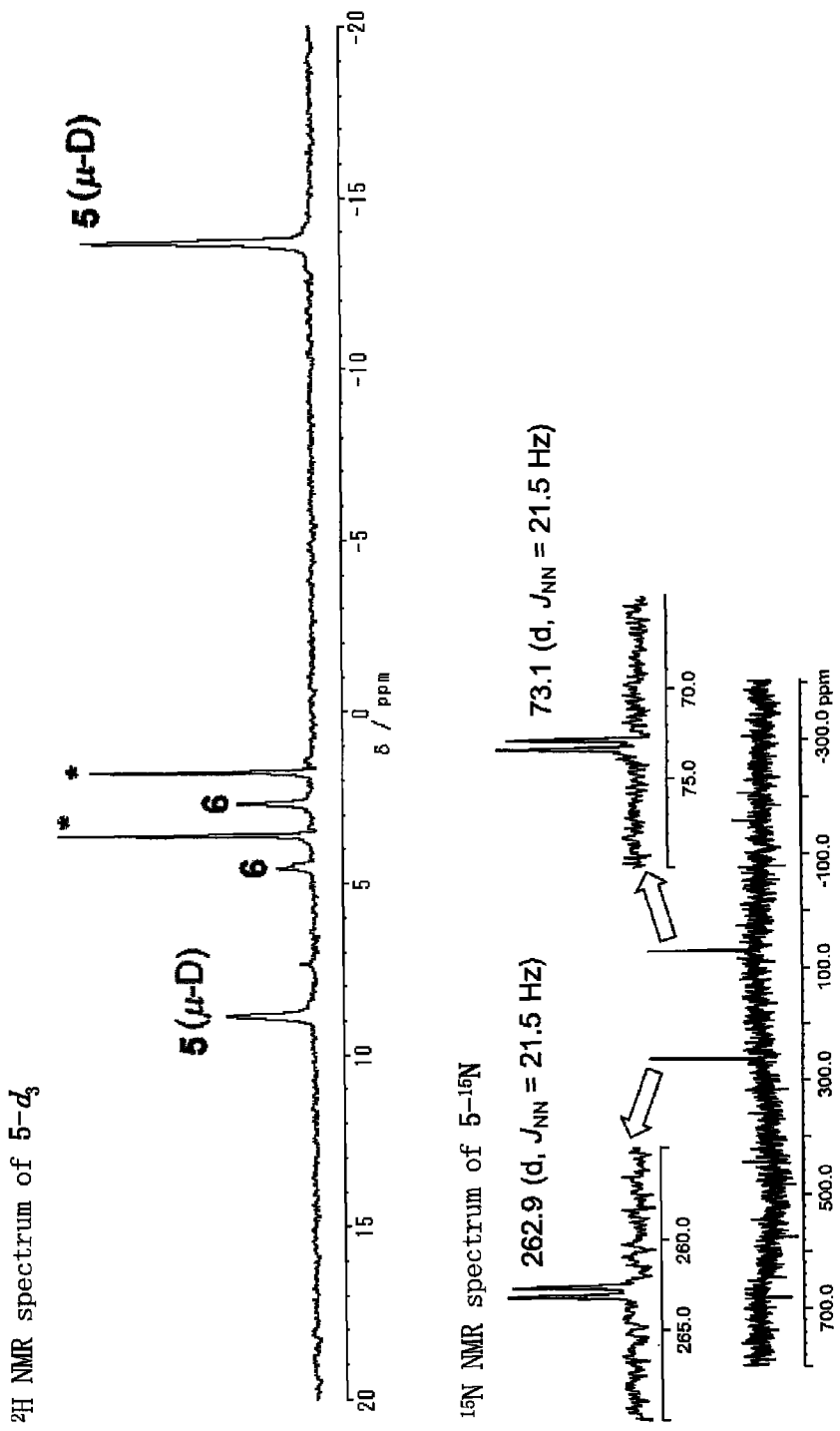
FIG. 9 shows the NMR spectrum of a complex molecule according to the example.
Figure 10:
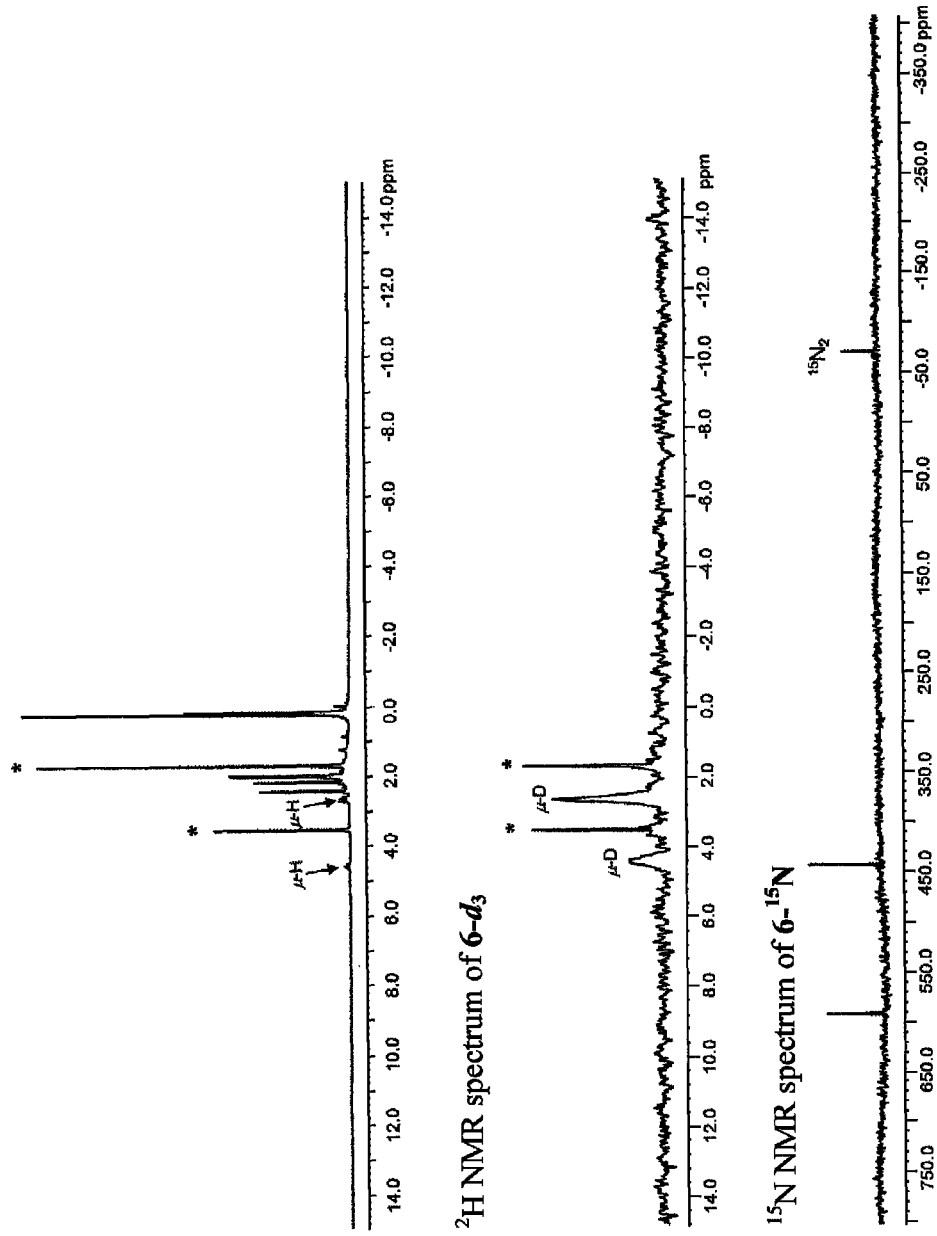
FIG. 10 shows the NMR spectrum of a complex molecule according to the example.

NMR data for the two reaction intermediates $(C_5Me_4SiMe_3)_3Ti_3(\mu-\eta^1:\eta^2:\eta^2-N_2)(\mu-H)_3]$ (intermediate 5) and $(C_5Me_4SiMe_3)_3Ti_3(\mu_3-N)(\mu-N)(\mu-H)_3]$ (intermediate 6) is as indicated below. FIG. 9 shows an NMR spectrum (5-$d_3$:62 MHz in THF, *THF-$d_8$, $-70°$ C./5-$^{15}$N: 60.81 MHz, THF-$d_8$, MeNO$_2$, $-30°$ C.) of the intermediate 5. FIG. 10 shows an NMR spectrum (6:400 MHz, THF-$d_8$, $-50°$ C./6-$d_3$: 62 MHz in THF, *THF-$d_8$, $-50°$ C./6-$^{15}$N: 60.81 MHz, THF-$d_8$, MeNO$_2$, $-50°$ C.) of the intermediate 6.

Intermediate 5: $^1$H NMR (THF-$d_8$, $-30°$ C.): 9.73 (s, 1H, Ti—H), 2.52 (s, 6H, $C_5Me_4SiMe_3$), 2.00 (s, 6H, $C_5Me_4SiMe_3$), 1.91 (s, 6H, $C_5Me_4SiMe_3$), 1.84 (s, 6H, $C_5Me_4SiMe_3$), 1.80 (s, 6H, $C_5Me_4SiMe_3$), 1.72 (s, 6H, $C_5Me_4SiMe_3$), 0.15 (s, 18H, $C_5Me_4SiMe_3$), $-0.10$ (s, 9H, $C_5Me_4SiMe_3$), $-13.80$ (s, 2H, Ti—H—Ti).

Intermediate 5-$^{15}$N: $^{15}$N NMR (60.81 MHz, THF-$d_8$, MeNO$_2$, $-30°$ C.): 73.1 (d, $J_{NN}$=21.5 Hz, N—N), 262.9 (d, $J_{NN}$=21.5 Hz, N—N).

Intermediate 5-$d_3$: $^2$H NMR (62 MHz, THF-$d_8$, $-70°$ C.): 8.86 (s, 1D, μ-D), $-13.72$ (s, 2D, μ-D).

Complex 6: $^1$H NMR (THF-$d_8$, $-70°$ C.): 4.65 (t, $J_{HH}$=28.0 Hz, 1H, Ti—H—Ti), 2.67 (d, $J_{HH}$=28.0 Hz, 2H, Ti—H—Ti), 2.47 (s, 6H, $C_5Me_4SiMe_3$), 2.20 (s, 6H, $C_5Me_4SiMe_3$), 2.07 (s, 6H, $C_5Me_4SiMe_3$), 2.02 (s, 12H, $C_5Me_4SiMe_3$), 1.74 (obscured by THF-$d_8$, $C_5Me_4SiMe_3$), 0.26 (s, 18H, $C_5Me_4SiMe_3$), 0.18 (s, 9H, $C_5Me_4SiMe_3$).

Complex 6-$^{15}$N: $^{15}$N NMR (60.81 MHz, THF-$d_8$, MeNO$_2$, $-50°$ C.): 593.4 (s, μ-N), 444.8 (s, μ-N).

Complex 6-$d^3$: $^2$H NMR (62 MHz, THF-$d_8$, $-50°$ C.): 4.56 (s, 1D, μ-D), 2.77 (s, 2D, μ-D).

(Ammonia Synthesis Process Involving the Use of a Complex)

A J. Young valve NMR sample tube was charged with the complex 7 (10 mg, 0.013 mmol: D in the reaction formula) thus obtained. After degassing, 1 atm of $^{15}N_2$ gas was added. The system was warmed to 160° C. for 24 hours. After the completion of the reaction, it was confirmed from the results of NMR that a complex 8 (E in the reaction formula) had been synthesized at a degree of conversion of 85% or higher. It should be noted that L in the reaction formula represents ($C_5Me_4SiMe_3$).

8: $^1$H NMR (400 MHz, $C_6D_6$, rt): 14.02 (s, 3H, μ-NH), 2.34 (s, 18H, $C_5Me_4SiMe_3$), 1.90 (s, 18H, $C_5Me_4SiMe_3$), 0.32 (s, 27H, $C_5Me_4SiMe_3$).

A new catalyst process of synthesizing ammonia from nitrogen and hydrogen by using the complexes 1, 7, and 8 as key catalysts is developed. For example, ammonia can be catalytically synthesized by pressurizing and heating the complex 8 with use of a mixture gas of nitrogen and hydrogen.

4. Example 2

(Synthesis of a Titanium-Lewis Acid Complex)

[Chem. 21]

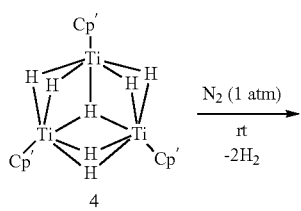

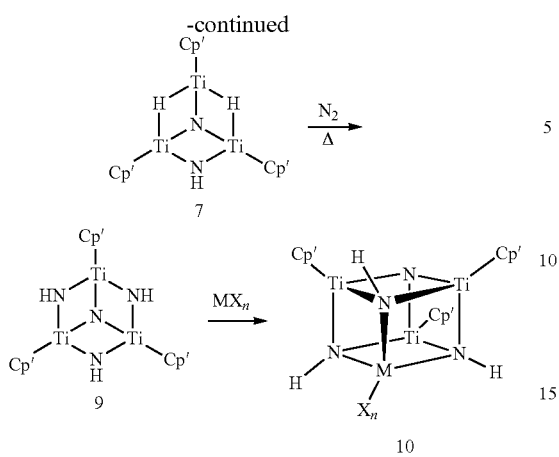

MX$_n$ = CuCl, ZnCl$_2$, SoCl$_3$ etc.

To the complex 4 obtained in Example 1, 1 atm of N$_2$ gas was added. The solution was kept at room temperature.

The addition of N$_2$ to the complex 4 caused the complex 4 to be converted to an intermediate 7 with the generation of H$_2$. To the intermediate 7, 1 to 20 atm of N$_2$ gas was further added to give a complex 9. To a toluene solution of the complex 9 (175 mg, 0.224 mmol) thus obtained, CuCl (copper chloride) (22.2 mg, 0.224 mmol) was added as a Lewis acid MXn. The mixture was stirred for 1 hour at room temperature. Then, the reaction solution was let stand still overnight at −35° C. to give a titanium-copper chloride complex 10 (MXn=CuCl) (162 mg, 0.184 mmol, in a yield of 82% with respect to the molar quantity of the complex 9) as reddish brown crystals.

Complex 10 (MXn=CuCl): $^1$H NMR (C$_6$D$_6$, rt): 12.03 (brs, 3H, NH), 2.23 (s, 18H, C$_5$Me$_4$SiMe$_3$), 1.86 (s, 18H, C$_5$Me$_4$SiMe$_3$), 0.33 (s, 27H, Si(CH$_3$)$_3$). $^{13}$C{$^1$H} NMR (C$_6$D$_6$, rt): 127.5 (s, C$_5$Me$_4$SiMe$_3$), 124.9 (s, C$_5$Me$_4$SiMe$_3$), 116.2 (s, ipso-C$_5$Me$_4$SiMe$_3$), 15.1 (s, s, C$_5$Me$_4$SiMe$_3$), 11.8 (s, C$_5$Me$_4$SiMe$_3$), 2.36 (s, C$_5$Me$_4$SiMe$_3$). $^{15}$N{$^1$H} NMR (40.52 MHz, toluene-d$_8$, MeNO$_2$, rt): 406.1 (s, μ$^3$-$^{15}$N), 21.9 (s, μ$^2$-$^{15}$NH). Calcd for C$_{36}$H$_{66}$ClCuN$_4$Si$_3$Ti$_3$: C, 49.03; H, 7.54; N, 6.35. found: C, 49.25; H, 7.48; N, 6.35.

Further, the same method was applied to give a titanium-zinc chloride complex 10 (MXn=ZnCl$_2$) (in a yield of 58% with respect to the molar quantity of the complex 9) as dark green crystals and a titanium-scandium chloride complex 10 (MXn=ScCl$_3$) (in a yield of 48% with respect to the molar quantity of the complex 9) as red crystals.

Complex 10 (MXn=ZnCl$_2$): $^1$H NMR (C$_6$D$_6$, rt): 2.14, 2.12, 2.09, 2.00, 1.97, 1.95 (s, 6×6H, C$_5$Me$_4$SiMe$_3$), 0.31 (s, 18H, Si(CH$_3$)$_3$), 0.29 (s, 9H, Si(CH$_3$)$_3$). NH protons were not observed. Calcd for C$_{36}$H$_{66}$Cl$_2$N$_4$Si$_3$Ti$_3$Zn: C, 47.04; H, 7.24; N, 6.10. found: C, 47.07; H, 7.05; N, 6.01.

Complex 10 (MXn=ScCl$_3$): $^1$H NMR (C$_6$D$_6$, rt): 12.82 (brs, 3H, NH), 2.36 (s, 18H, C$_5$Me$_4$SiMe$_3$), 2.20 (s, 18H, C$_5$Me$_4$SiMe$_3$), 0.32 (s, 27H, Si(CH$_3$)$_3$).

(Ammonia Synthesis Process Based on the Addition of a Nitrogen-Hydrogen Gas to a Titanium-Lewis Acid Complex)

[Chem. 22]

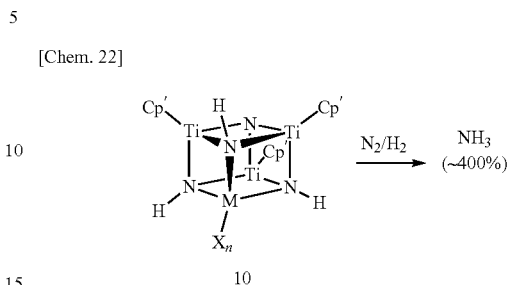

The complex 10 (MXn=CuCl) was taken as a solid (11.9 mg, 13.5 μmol) into a high-pressure flow reaction apparatus, and 5 atm of N$_2$ gas and 15 atm of H$_2$ gas were added. The reaction was allowed to take place for 4 days at 160° C. The gas component was quantified by an indophenol method and ion chromatography analysis to give ammonia (53.8 μmol, 399%) in a yield of approximately 400% with respect to the molar quantity of the complex 10.

Further, with use of a catalyst in which the complex 10 (12.5 mg, 14.2 μmol) was supported on a carrier material such as silica (such as MCM-41) or alumina, hydrogen at normal pressures was allowed to flow for 5 hours at a temperature of 100° C., whereby ammonia (55.5 μmol, 391%) was obtained in a yield of approximately 400% with respect to the molar quantity of the complex 10.

(Functionalization of Nitrogen)

[Chem. 23]

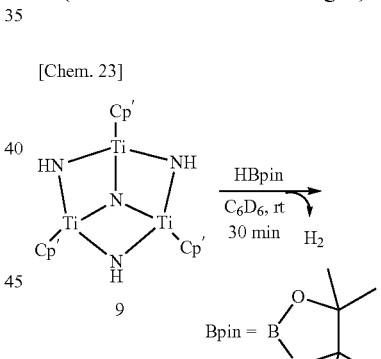

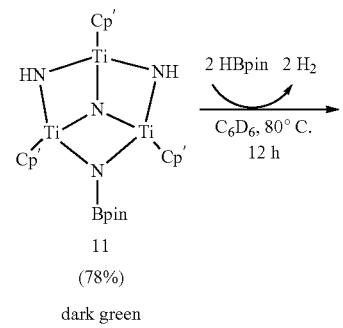

-continued

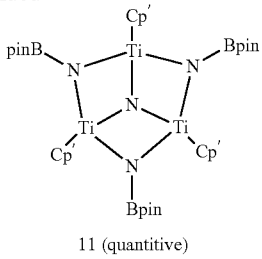

11 (quantitive)

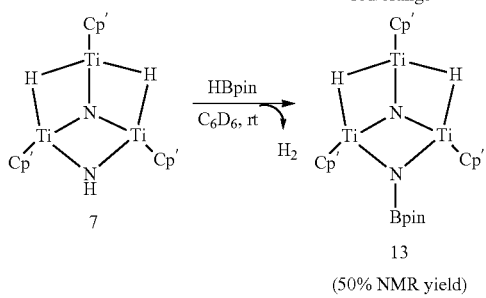

(50% NMR yield)

The complex 9 (10 mg, 0.013 mmol) obtained through the reaction between the complex 4 and nitrogen was allowed to react with pinacol borane (HB$_{pin}$) (36 mg, 0.28 mmol) for 30 minutes at room temperature in the presence of C$_6$D$_6$ to give a dark green complex 11 having a boron bond on nitrogen (in a yield of 78% with respect to the molar quantity of the complex 9). Then, the complex 11 was allowed to react with pinacol borane (HB$_{pin}$) for 12 hours at 80° C. in the presence of C$_6$D$_6$ to give a red or orange complex 12. Further, the complex 7 (10 mg, 0.013 mmol) obtained through the reaction between the complex 4 and nitrogen was allowed to react with pinacol borane (HB$_{pin}$) (16 mg, 0.13 mmol) for 30 minutes at room temperature in the presence of C$_6$D$_6$ to give a complex 13 having a boron bond on nitrogen (in a yield of 50% with respect to the molar quantity of the complex 7).

INDUSTRIAL APPLICABILITY

The present invention is applicable to fixation of dinitrogen or taking out of dinitrogen that have been fixed.

The invention claimed is:

1. A complex represented by formula (1A) or (1B) or a cationic or anionic complex from the complex:

[Chem. 1]

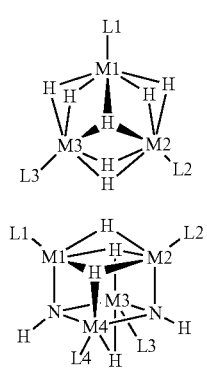

wherein M1 to M4 (M1 to M3 in the case of formula (1A)) are each independently Ti, Zr, Hf, V, Nb, Ta, Cr, Mo, or W, and L1 to L4 (L1 to L3 in the case of formula (1A)) are each independently a ligand selected from the group consisting of a ligand (Cp) including a substituted or unsubstituted cyclopentadienyl derivative, a diphenylamine ligand, a diphenylphosphine ligand, and a carboimideamide ligand.

2. The complex as set forth in claim 1, wherein L1 to L4 (L1 to L3 in the case of formula (1A)) of formulas (1A) and (1B) are identical ligands each of which is represented by formula (2):

[Chem. 2]

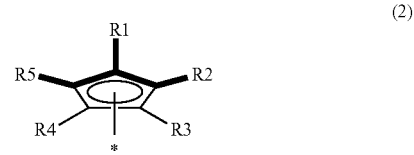

wherein R1 to R5 are each independently a hydrogen atom that binds to a carbon atom constituting the skeleton of the cyclopentadienyl ring; a C1-C20 hydrocarbyl group; or a substituted metalloid group in which a C1-C20 hydrocarbyl group, an amide group, a phosphide group, and/or an alkoxide group has/have been substituted, ⋇ is a bond with M1 to M4 (M1 to M3 in the case of formula (1A)), and two to five of R1 to R5 are the hydrocarbyl group or substituted metalloid group, and wherein one of the carbon atoms constituting the skeleton of the cyclopentadienyl ring may be substituted by a 14th-group atom (excluding a carbon atom and a lead atom) or a 15th-group atom.

3. The complex as set forth in claim 2, wherein, in formula (2), all of R1 to R5 are methyl groups, or four of R1 to R5 are methyl groups and the other one of R1 to R5 is a trialkylsilyl group.

4. The complex as set forth in claim 1, wherein each of M1 to M4 (M1 to M3 in the case of formula (1A)) of formulas (1A) and (1B) is Ti.

5. A complex as set forth in claim 1, the complex being represented by formula (1A).

6. A complex having nitrogen atoms incorporated therein by bringing a complex as set forth in claim 1 and nitrogen molecules into contact with each other.

7. The complex as set forth in claim 6, the complex being a complex represented by formula (3) or a cationic or anionic complex from the complex:

[Chem. 3]

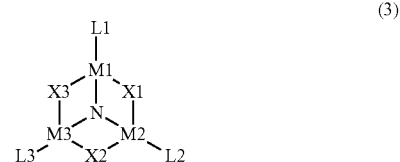

wherein M1 to M3 and L1 to L3 are identical to those of formula (1A), X1 to X3 are each —H— or —N(H)—, and one or two of X1 to X3 are —N(H)—, and in one or more —N(H)—'s, H may be substituted by a boryl group, a silyl group, or an alkyl group.

8. A complex represented by formula (3') or a cationic or anionic complex from the complex:

[Chem. 4]

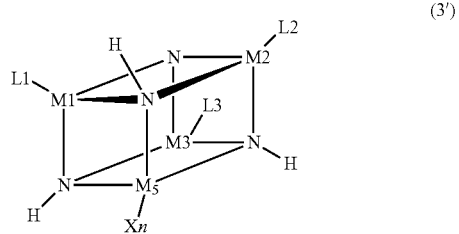

(3')

wherein M1 to M3 are each independently Ti, Zr, Hf, V, Nb, Ta, Cr, Mo, or W, L1 to L3 are each independently a ligand selected from the group consisting of a ligand (Cp) including a substituted or unsubstituted cyclopentadienyl derivative, a diphenylamine ligand, a diphenylphosphine ligand, and a carboimideamide ligand, M5 is Cu, Zn, Sc, or Y, X is F, Cl, Br, I, or —$OSO_2CF_3$, and n (which indicates the number of X's) is an integer represented by p-3 (where p is the coordination number of M5).

9. A method for synthesizing ammonia, comprising the step of bringing hydrogen molecules and nitrogen molecules into contact with a complex as set forth in claim 1.

10. A fixed bed for use in ammonia synthesis, comprising a complex as set forth in claim 1, the complex being fixed.

11. A method for synthesizing ammonia, comprising the step of brining hydrogen molecules into contact with a complex as set forth in claim 6.

12. A method for synthesizing ammonia, comprising the step of brining hydrogen molecules into contact with a complex as set forth in claim 7.

13. A method for synthesizing ammonia, comprising the step of bringing hydrogen molecules and nitrogen molecules into contact with a complex as set forth in claim 8.

14. A fixed bed for use in ammonia synthesis, comprising a complex as set forth in claim 6, the complex being fixed.

15. A fixed bed for use in ammonia synthesis, comprising a complex as set forth in claim 7, the complex being fixed.

16. A fixed bed for use in ammonia synthesis, comprising a complex as set forth in claim 8, the complex being fixed.

\* \* \* \* \*